(12) United States Patent
Berens et al.

(10) Patent No.: US 8,710,093 B2
(45) Date of Patent: *Apr. 29, 2014

(54) SYNTHESIS OF AMINES AND INTERMEDIATES FOR THE SYNTHESIS THEREOF

(75) Inventors: Ulrich Berens, Binzen (DE); Oliver Dosenbach, Bad Bellingen (DE); Daniel Sprenger, Basel (CH)

(73) Assignee: BASF SE Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/459,290

(22) Filed: Apr. 30, 2012

(65) Prior Publication Data

US 2012/0220782 A1 Aug. 30, 2012

Related U.S. Application Data

(62) Division of application No. 13/098,535, filed on May 2, 2011, and a division of application No. 10/539,151, filed as application No. PCT/EP03/50992 on Dec. 12, 2003, now Pat. No. 7,645,886.

(30) Foreign Application Priority Data

Dec. 20, 2002 (EP) .................................. 02 406 128

(51) Int. Cl.
*A61K 31/404* (2006.01)
*C07D 209/38* (2006.01)

(52) U.S. Cl.
USPC .......................................... 514/418; 548/485

(58) Field of Classification Search
USPC ....................................................... 548/485
See application file for complete search history.

(56) References Cited

U.S. PATENT DOCUMENTS

| | | | |
|---|---|---|---|
| 3,577,430 A | 5/1971 | Plostnieks | |
| 4,650,810 A * | 3/1987 | Bays et al. | 514/415 |
| 4,855,314 A | 8/1989 | Oxford et al. | |
| 5,607,960 A | 3/1997 | Wythes | |
| 5,856,510 A | 1/1999 | Meng et al. | |
| 5,998,438 A | 12/1999 | Slassi et al. | |
| 6,187,805 B1 | 2/2001 | Pineiro et al. | |
| 6,329,390 B1 | 12/2001 | Slassi et al. | |
| 6,489,512 B1 | 12/2002 | Hicks et al. | |
| 7,968,730 B2 | 6/2011 | Berens et al. | |

FOREIGN PATENT DOCUMENTS

| | | |
|---|---|---|
| FR | 79476 | 12/1962 |
| GB | 981192 | 1/1965 |
| GB | 2168347 | 6/1986 |
| GB | 2186874 | 8/1987 |
| JP | 61-151172 | 7/1986 |
| JP | 61-158960 | 7/1986 |
| JP | 62-228056 | 10/1987 |
| JP | 62-228057 | 10/1987 |
| JP | 08-507083 | 7/1996 |
| JP | 2002-520412 | 7/2002 |
| JP | 2011-168608 | 9/2011 |
| WO | 93/00333 | 1/1993 |
| WO | WO 9414771 A1 * | 7/1994 |
| WO | 95/09858 | 4/1995 |
| WO | 97/43281 | 11/1997 |
| WO | 99/02493 | 1/1999 |
| WO | 02/28831 | 4/2002 |
| WO | 02/062290 | 8/2002 |
| WO | WO 02078693 A2 * | 10/2002 |
| WO | 2005/075422 | 8/2005 |

OTHER PUBLICATIONS

Hoshino et al. (Ann. 1935, 520, 19-30).*
Bosch et al., Tetrahedron, 2001, 57, 1041-1048.*
Andersen et al., J. Med. Chem. 1996, 39, 3723-3738.*
Wu, T.Y.H. et al., "A Versatile Linkage Strategy for Solid-Phase Synthesis of N,N-Dimethyltryptamines and B-Carbolines", Organic Letters, 2002, vol. 4, No. 23, pp. 4033-4036.
Hansch, C. et al., "Searching for Allosteric Effects Via QSARs, Bioorganic & Medicinal Chemistry", 2001, vol. 9, No. 2, pp. 283-289.
Meng, C.Q. et al., "5-Thienyltryptamine Derivatives as Serotonin 5-HT1B/1D Receptor Agonists: Potential Treatments for Migraine", Bioorganic & Medicinal Chemistry Letters, 2000, vol. 10, No. 9, pp. 903-905.
Glennon, R.A., et al., "5-HT6 Serotonin Receptor Binding of Indolealkylamines: A Preliminary Structure-Affinity Investigation", Medicinal Chemistry Research, 1999, vol. 9, No. 2, pp. 108-117.

(Continued)

*Primary Examiner* — Shawquia Young
(74) *Attorney, Agent, or Firm* — Shruti Costales

(57) ABSTRACT

The invention relates in a first embodiment to a method for the manufacture of esters of the formula I,

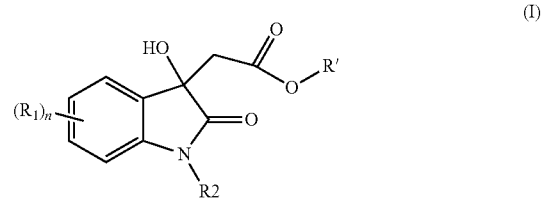

(I)

or especially of amides of the formula II,

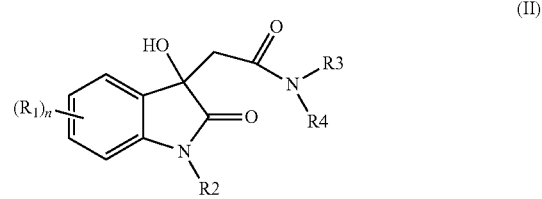

(II)

wherein the symbols have the meanings given in the specification, as well as other intermediates and compounds useful in the synthesis of tryptamines and other substances mentioned in the title. The synthesis methods and intermediates are useful in the synthesis of pharmaceuticals.

10 Claims, No Drawings

(56) References Cited

OTHER PUBLICATIONS

Demerson, C.A., et al., "Etodolic Acid and Related Compounds. Chemistry and Antiinflammatory Actions of Some Potent Di- and Trisubstituted 1,3,4,9-Tetrahydropyrano[3,4-b]indole-1-acetic Acids", Journal of Medicinal Chemistry, 1976, vol. 19, No. 3, pp. 391-395.

Kinashi, H, et al., "Possible Metabolic Intermediates from IAA to β-Acid in Rice Bran", Agricultural and Biological Chemistry, 1976, vol. 40, No. 12, pp. 2465-2470.

Soli, R.M. et al., "Multigram Preparation of 1,8-Diethyl-7-hydroxy-1,3,4,9-tetrahydropyrano-[3,4-13]indole-1-acetic Acid, a Phenolic Metabolite of the Analgesic and Antiinflammatory Agent Etodolac", Journal of Organic Chemistry, 1988, vol. 53, No. 12, pp. 2844-2847.

Tadera, K. et al., "Isolation and Structure of a New Vitamin B6 Conjugate in Rice Bran", Journal of Food Science, 1991, vol. 56, No. 1, pp. 268-269.

Kato, T. et al., "In vitro oxidation of indoleacetic acid by crude enzyme from rice husk—an aspect of preharvest sprouting", Heterocycles 1998, vol. 47, No. 1, pp. 497-500.

Garden, S. J. et al., "A versatile synthetic methodology for the synthesis of tryptophols", Tetrahedron, 2002, vol. 58, pp. 8399-8412.

Canoira, L. et al., "Synthesis of indole and oxindole derivatives from N-.beta.-alkenyl-o-chloroanilines and N-.beta.-alkenyl-o-chloroanilides with tetrakis (triphenylphosphine)nickel(0) and zerovalent pyridine-nickel complexes", Journal of Chemical Research, Synopses, 1988, vol. 2, pp. 68-69.

Revial, G. et al., "Aromatization of 1, 6, 7, 7a-Tetrahydro-2H-indol-2-ones by a Novel Process. Preparation of Key-Intermediate Methyl 1-Benzyl-5-methoxy-1H-indole-3-acetate and the Syntheses of Serotonin, Melatonin, and Bufotenin", Journal of Organic Chemistry, 2002, vol. 67, No. 7, pp. 2252-2256.

Beccalli, E. M. et al., "Synthesis of [a]Annulated Carbazoles from Indol-2,3-dione", Tetrahedron, 1993, vol. 49, No. 21, pp. 4741-4758.

* cited by examiner

SYNTHESIS OF AMINES AND INTERMEDIATES FOR THE SYNTHESIS THEREOF

This application is a divisional of copending U.S. patent application Ser. No. 13/098,535, filed on May 2, 2011, which is a divisional of U.S. patent application Ser. No. 10/539,151, filed on Jun. 16, 2005, now issued as U.S. Pat. No. 7,645,886, which is a 371 of international app. No. PCT/EP2003/50992, filed Dec. 12, 2003, which claims priority to EP 02406128.5, filed Dec. 20, 2002, all of which are herein incorporated by reference.

SUMMARY OF THE INVENTION

The present invention provides a novel process (=method) for the manufacture of derivatives, especially precursors, of tryptamine, horsfiline or coerulescine, novel partial reactions and novel intermediates. The derivatives or precursors of tryptamine, horsfiline and coerulescine are useful e.g. in the pharmaceutical area.

BACKGROUND OF THE INVENTION

Derivatives of tryptamine 1

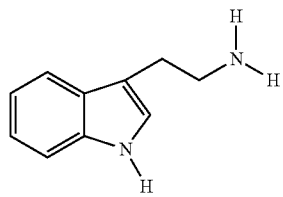

have been synthesized from substituted anilines. Some pertinent anilines are prepared from 4-nitro benzyl chloride (precursors for anti migraine pharmaceuticals such as Sumatriptan 2 see: DE 3,320,521, U.S. Pat. No. 4,816,470, Almotriptan 3 see: Res. Disci. 1998, 412, 1088, Rizatriptan 4 see: EP 0497512A2) or Zolmitriptan 5 from 4-nitro phenyl alanine see: WO 91/18897.

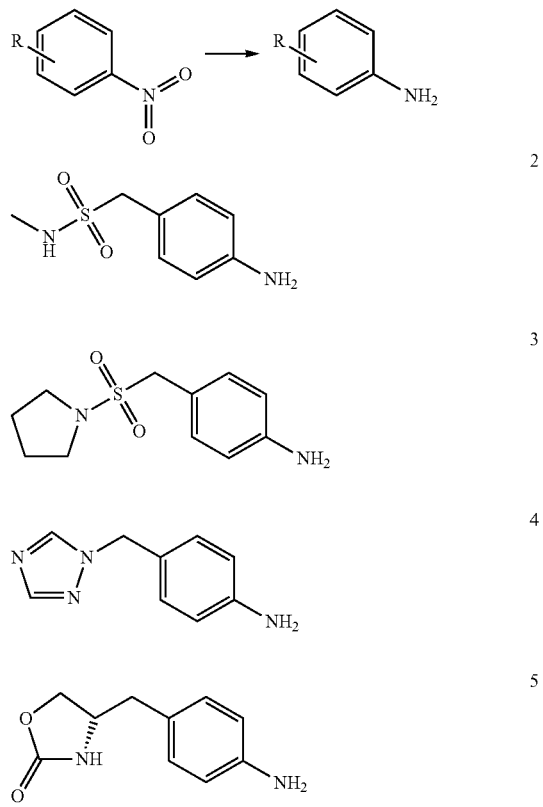

A variety of strategies have been disclosed for the conversion of the anilines 2, 3, 4 or 5 into the related tryptamine derivative 1. In the most common approach (scheme 2), the aniline A is converted into the corresponding phenyl hydrazine B. This is then reacted with a 4-halogeno-butyraldehyde derivative C (e.g. the dimethyl acetal (see: U.S. Pat. No. 4,816,470) or the sodium sulfite addition product (see: EP 462 837 A2 or U.S. Pat. No. 5,103,020)) or with a derivative of 4-amino butyraldehyde to give tryptamine D. Methylation of the amine of D provides the corresponding drug H. Alternatively, aniline A may be converted into indole E. A variety of pathways for the subsequent conversion of E into H is disclosed in U.S. Pat. No. 5,037,845.

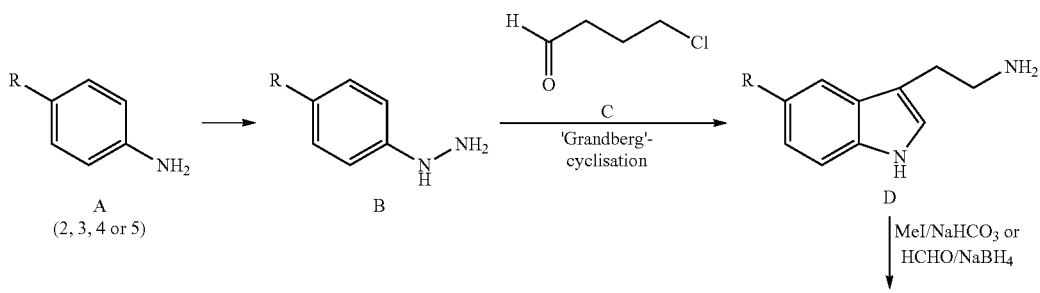

-continued

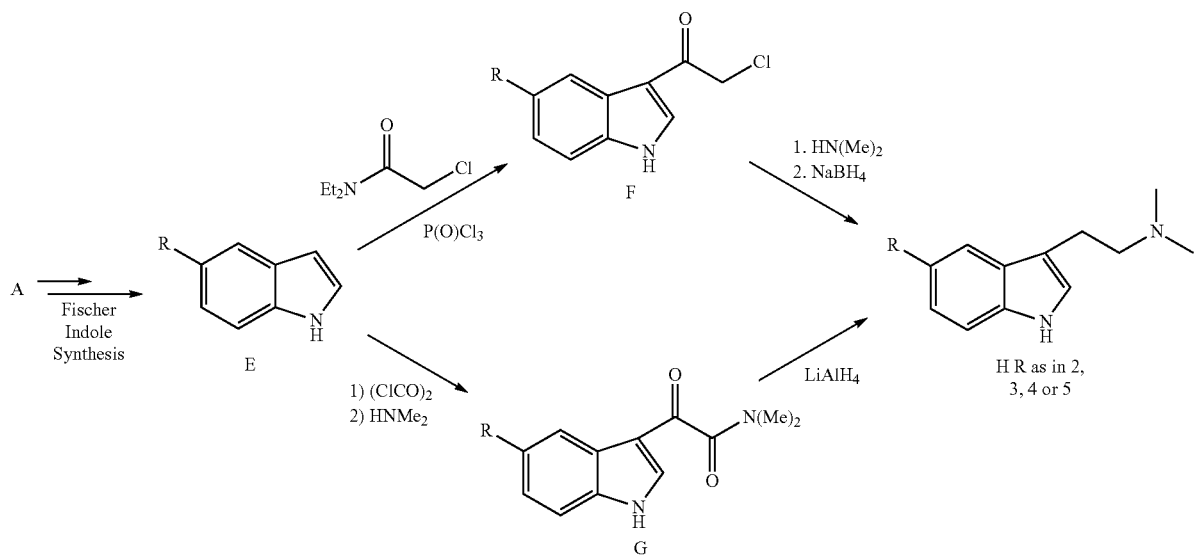

One important problem regarding these approaches is the conversion of aniline A into phenyl hydrazine B. The reduction of the diazonium salt derived from A has been performed using tin(II)chloride in a three to five-fold excess. A range of environmentally more suitable reducing agents has been identified, and is claimed in patent application WO 01/34561.

For a detailed account of problems in the preparation of the phenyl hydrazine that is derived from 2 and its transformation into Sumatriptan see: *Heterocycles* 1998, 48, 1139. Similar problems can be expected for phenyl hydrazines that are derived from anilines 3, 4, and 5. Thus, the use of α-keto-δ-valerolactone as the carbonyl component for the Fischer-cyclisation has been suggested as an alternative, see: SK 280586B (Applicant: QUMICA SINT S A (ES); VITA INVEST, Publication date 2000-4-10).

Scheme 3: Alternative Carbonyl compounds for the Fischer cyclisation

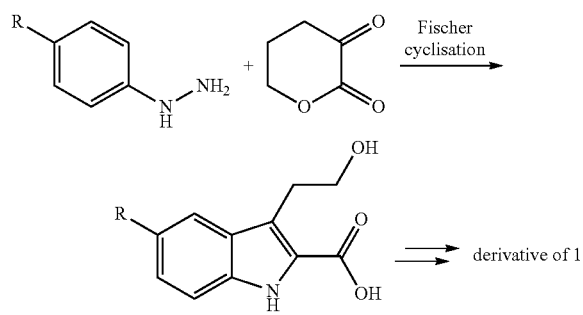

A quite different approach to synthesize Sumatriptan also requires aniline 2, but the preparation of the phenyl hydrazine is avoided, see: *Heterocycles* 2000, 53, 665. Here, the diazonium salt from 2 is reacted with a β-ketocarboxylic acid ester, and the formed hydrazone is cyclised to the indole 2-carboxylic acid which is decarboxylated to a derivative of 1.

Scheme 4: Alternative to the preparation of a phenyl hydrazone (synthesis of the N,N-dimethylpropyl-malonic acid ethyl ester is inconvenient)

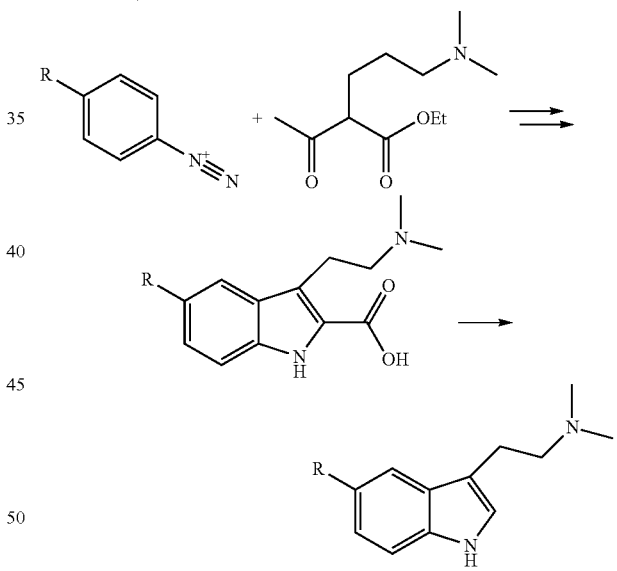

A major problem of the Fischer indolisation is that frequently only low yields of the indole are obtained due to the lack of stability of the product under the rather strongly acidic reaction conditions. Moreover, a problem of the Grandberg indolisation is that the reductive di-methylation of the primarily formed tryptamine in an alternative way is prone to low yields as side reactions such as formation of carbazoles and methylation of the indole nitrogen can take place. A solution to both of these problems is provided by using a derivative of N,N-dimethyl-4-aminobutyraldehyde in a modified Fischer indolisation protocol, see: *J. Org. Chem.* 1994, 59, 3738.

In all synthesis variants for derivatives of tryptamine 1 presented so far, the nature of the final product is determined early at the aniline stage. The final product is then obtained through the identical steps of hydrazine synthesis and Fischer indole cyclisation with all the described limitations. The present invention describes a route to late common intermediates for the synthesis of derivatives of tryptamine such as 1 which avoids both the synthesis of phenyl hydrazones and variations of the Fischer indolisation.

The reaction of isatin (or a derivative) with malonic acid in acetic acid, either in the presence or absence of sodium acetate, furnishes the quinolone carboxylic acid 6 instead of the expected product 7, see *J. Chem. Soc.* 1926, 2902 and *Chem. Ber.* 1914, 47, 354.

Scheme 5: Condensation of isatin with malonic acid in acetic acid

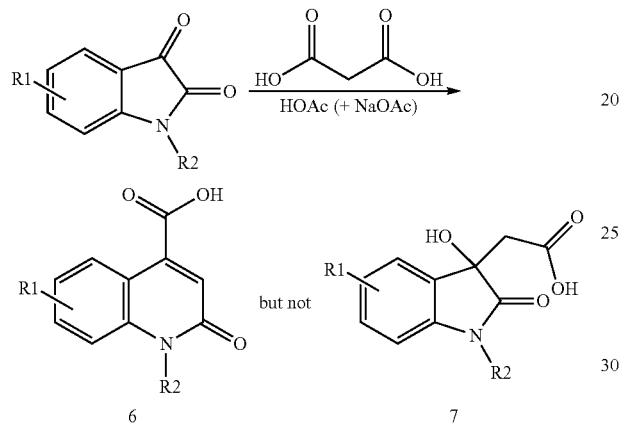

6        7

However, compounds such as 7 are known, and have been prepared for example by reacting isatin or a derivative of it with the Reformatzky reagent of a derivative of bromo acetic acid, see *Chem. Ber,* 1962, 95, 1138 or *Tetrahedron* 1967, 23, 901 or with a 15-fold excess of the lithium enolate of tert-butyl acetate, see *J. Org. Chem.* 1988, 53, 2844. Derivatives of 7 also have been prepared by the condensation of an isatin with methyl acetimidate and subsequent hydrolysis, see *Liebigs Ann. Chem.* 1967, 701, 139 or by the oxidation of the enolate of a 3-methoxycarbonylmethyl-2-oxo-2,3-dihydro-1H-indol-5-yl derivative with Davies reagent, see *Heterocycles* 1998, 47, 49.

Analogues of 7 have been obtained when a derivative of isatin wherein $R_2$ is a substitutent hydrogen or ethyl was reacted with malonic acid in pyridine (see Garden et al., Tetrahedron 58, 8399-8412 (2002)). In this case the pyridinium salt 8 was obtained, from which the corresponding acid 9 was obtained simply by acidification with hydrochloric acid.

Scheme 6: Condensation of isatin with malonic acid in pyridine (R1 = hydrogen or lower alkyl)

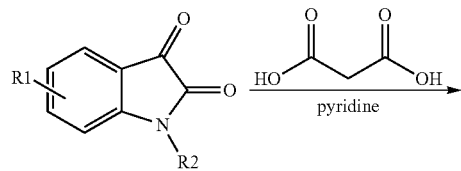

-continued

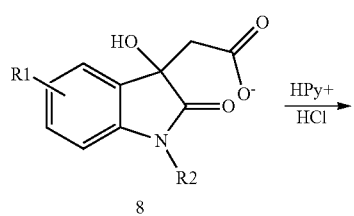

8

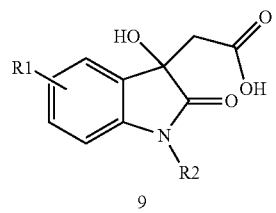

9

9 was then transformed into the corresponding ester in the presence of methanol and the ester then reduced with sodium borohydride to yield the corresponding tryptophol 9a:

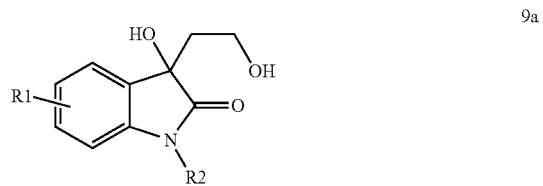

However, it was observed that when $R_2$ is hydrogen (non-N-alkylated isatin) the corresponding esterification does not work. Therefore an alternative procedure employing the potassium salt of the mono-ethyl malonyl ester with 7-ethylisation in a mixture of pyridine, acetic acid and ethanol under reflux was used which gave the corresponding ester that could then be reduced.

GENERAL DESCRIPTION OF THE INVENTION

It has now been found surprisingly that when a compound such as 8 is reacted with an appropriate nitrogen base, especially a tertiary amine, such as triethyl amine (given in scheme 7 as an example only), it becomes sufficiently nucleophilic to react either with an active carbonic ester such as 10 (wherein R' is, for example, lower alkyl) or an active amide such as chloro amido carbonic acid derivative 12 (wherein $R_3$ and $R_4$ are unsubstituted or substituted alkyl or together form a lower alkylene bridge) to give an ester such as 11 or an N,N-disubstituted alkylamide derivative such as 13 of 9. Very advantageously and surprisingly, the condensation step can conveniently be combined with the derivatisation step, which allows to obtain esters 11 or especially amides 13 of 9 in a one pot reaction. In this context triethylamine cannot be used for the addition reaction of malonic acid to isatin. (In formulae II and 13 and their precursors in brackets, R1 represents one or more substitutents and R2 a nitrogen substituent).

Scheme 7: Synthesis of esters 11 and amides 13 of 9

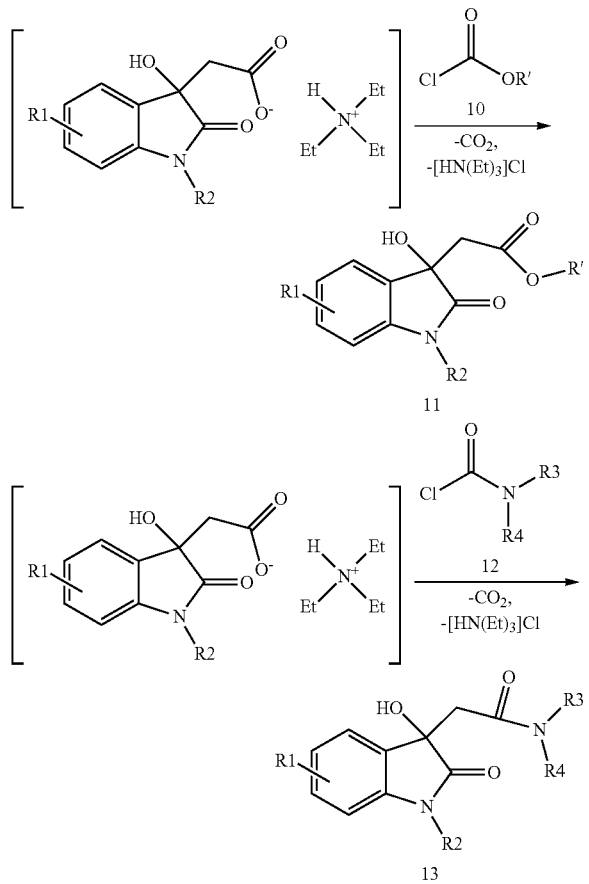

Compounds such as 9, 11 or 13 are also valuable starting materials for further unprecedented conversion reactions into various derivatives or precursors of tryptamine 1 which are described in more detail below.

DETAILED DESCRIPTION OF THE INVENTION

The invention relates in a first embodiment to a method for the manufacture of esters of the formula I,

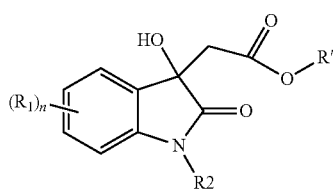

wherein n is a number from 0 to 4,
each $R_1$ is, independently of the other substituents $R_1$, unsubstituted or substituted alkyl, unsubstituted or substituted aryl, unsubstituted or substituted heterocyclyl, alkylsulfonyl, alkyl sulfonyl, sulfonyl alkyl, unsubstituted, N-mono- or N,N-disubstituted or unsubstituted aminosulfonyl alkyl, hydroxy, mercapto, nitro, halogen, cyano, carboxamido, N-mono- or N,N-disubstituted carboxamido, unsubstituted or substituted alkoxycarbonyl, unsubstituted or substituted alkoxy, formyl or other alkanoyl, unsubstituted or substituted alkenyl or unsubstituted or substituted alkynyl;

R2 is hydrogen or unsubstituted or substituted alkyl, unsubstituted or substituted alkoxycarbonyl, unsubstituted or substituted arylsulfonyl, unsubstituted or substituted alkylsulfonyl, unsubstituted or substituted aryl, carbamoyl or N-mono- or N,N-disubstituted carbamoyl, silyl substituted by three moieties independently selected from unsubstituted or substituted alkyl and substituted or unsubstituted aryl, or acyl, and R' is unsubstituted or substituted alkyl,
or especially of amides of the formula II,

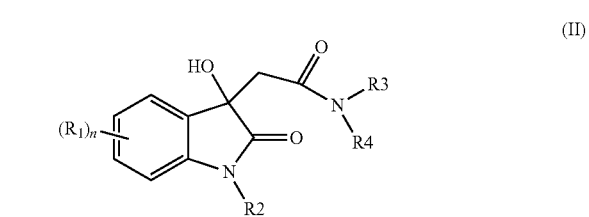

wherein n, $R_1$ and R2 are as defined under formula I and R3 and R4 are, independently of each other, unsubstituted or substituted alkyl or together form an unsubstituted or substituted alkylene bridge (thus forming a ring with the binding nitrogen) or an alkylene bridge to which a phenyl or a $C_3$-$C_8$-cycloalkyl ring is condensed at two vicinal carbon atoms of the alkylene bridge where a starting material of the formula III,

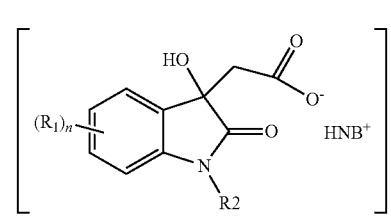

wherein n, $R_1$ and R2 have the meanings given under formula I and NB is a tertiary nitrogen base where the nitrogen is not part of a ring,
is reacted
(a) for the synthesis of an ester of the formula I with an active carbonic ester of the formula IV,

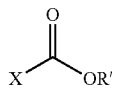

wherein X is halogen and R' is as defined under formula I, to give the corresponding ester of the formula I, or
(b) for the synthesis of an amide of the formula II with an active amido carbonic acid derivative of the formula V,

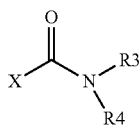

wherein X is halogen and R3 and R4 are as defined under formula II, to give the corresponding compound of the formula II.

Further to the above definitions, $R_1$ may also be unsubstituted or substituted cycloalkyl, alkanoyloxy, carboxyhydrazido, N-mono- or N,N-disubstituted or unsubstituted amino, unsubstituted or substituted hydrazino, or a residue of a boronic acid or an ester thereof. Such a boronic acid residue preferably conforms to the formula

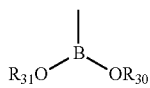

wherein $R_{30}$ and $R_{31}$ independently are hydrogen or a radical of an alcohol, e.g. lower alkyl, or together are $C_2$-$C_8$alkylene; preferred $R_{30}$ and $R_{31}$ independently are hydrogen or a residue of a sterically hindered alcohol such as isopropanol or pinakol.

In an especially preferred method, NB is a tri-lower alkylamine, especially triethylamine. The compound of the formula III is preferably obtained by reaction of an isatine derivative of the formula VI,

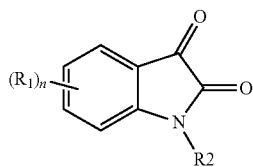

wherein n, $R_1$ and R2 have the meanings given under formula I, with malonic acid in the presence of a pyridine, especially pyridine and/or one or more picolines, in the absence or presence of a N,N-di-(lower alkyl)-lower alkanoylamide, a lower alkanol, e.g. methanol or ethanol, or a di-lower alkylsulfoxide, e.g. dimethylsulfoxide, especially N,N-dimethyl formamide, advantageously in the presence of ethyl acetate as a cosolvens, followed by conversion into the salt of the base NB given in formula III
by conversion of the resulting product of the formula III*,

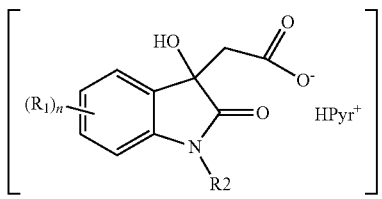

wherein n, $R_1$ and R2 have the meanings given under formula I and HPyr$^+$ is the respective cation resulting from a pyridine as mentioned above.

Preferably, the reaction of the compound of the formula VI with malonic acid in the presence of a pyridine and optionally a co-solvent as defined above, the subsequent conversion into the salt of the formula III with the base NB and reaction a) or b) above take place in the same reaction vessel (one pot synthesis).

The products of the formulae I or II can then be subjected to a number of novel, unprecedented reactions that yield various products useful in the synthesis of known or novel tryptamine derivatives with e.g. pharmacological useful properties.

In a first novel reaction, an amide of the formula II wherein n is zero and thus $R_1$ is absent is converted to a compound of the formula VII,

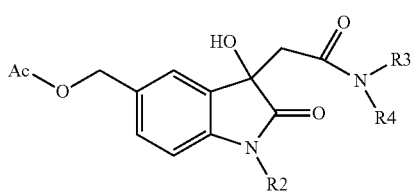

wherein Ac is acetyl and R2, R3 and R4 have the meanings indicated for compounds of the formula II with the proviso that in the compound of the formula II and of the formula VII, R2 is other than hydrogen, preferably unsubstituted or substituted alkyl;
by the reaction with formaldehyde or a precursor thereof in the presence of acetic acid, and preferably an acidic catalyst, thus yielding a new tryptamine precursor.

In a further embodiment of the invention, the compound of the formula VII is then transformed into the corresponding free alcohol of the formula VIII,

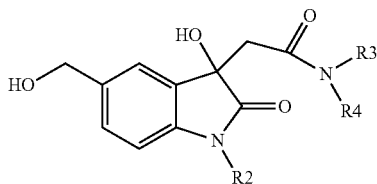

wherein R2, R3 and R4 are as defined under formula VII, another novel class of tryptamine precursors. This conversion is preferably effected by hydrolysis or transesterification.

In another embodiment of the invention, the alcohol of the formula VIII is then
reacted with an oxidising agent to give the corresponding compound of the formula IX (a compound of the formula II wherein $R_1$ is formyl in para position to the oxindole ring nitrogen)

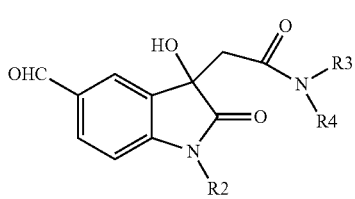

wherein R2, R3 and R4 have the meanings given under formula VII, again a novel intermediate in the synthesis of tryptanes. Preferred oxidising agent is $MnO_2$.

In another embodiment of the invention, a compound of the formula II wherein R2 has one of the meanings given above other than hydrogen is reacted with a dehydrating agent to give a compound of the formula Xa,

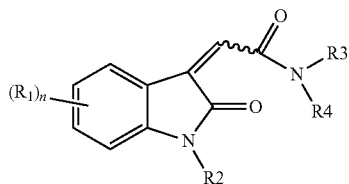

(Xa)

wherein n, $R_1$ and R2 are as defined under formula I and R3 and R4 are, independently of each other, unsubstituted or substituted alkyl, especially lower alkyl or phenyl lower alkyl, or together form an unsubstituted or substituted alkylene bridge, especially an unsubstituted or lower alkyl substituted lower alkylene bridge (thus forming a ring with the binding nitrogen).

In still another embodiment of the invention, the compound of the formula Xa is then reduced in the presence of a reductant to a compound of the formula Xb,

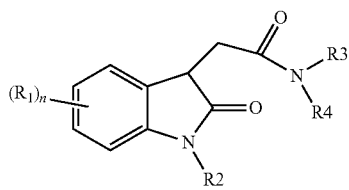

(Xb)

wherein n, $R_1$, R2, R3 and R4 are as defined for a compound of the formula II.

In an alternative embodiment of the invention, a compound of the formula Xb as just described is obtained by hydrogenation of the benzylic 3-hydroxy group in a compound of the formula II as just defined.

A compound of the formula Xb, e.g. as obtained in the above reactions, can surprisingly be converted to a Spiro oxindole of the formula XI by reaction with formaldehyde or a precursor thereof (e.g. paraformaldehyde):

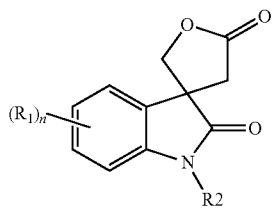

(XI)

Following the method of the invention, these compounds are readily accessible; they are useful as precursors for horsfiline or coerulescine or derivatives thereof (J. Org. Chem. 66, 8447, 2001, or Org. Lett. 3, 4193, 2001).

In the novel compounds of the present invention and in the compounds used and prepared in the process steps of the present invention (including educt compounds, e.g. of the formula II as described below), the substitutents and symbols, as far as present in the compounds of the formulae I to V, may have the following meanings:

n is an integer from 0 to 3, preferably from 0 to 2;

each $R_1$ is, independently of the other substituents $R_1$, lower alkyl, lower alkyl substituted by up to three moieties selected from N,N-di-lower alkylamino, N-phenyl-lower alkylamino, N,N-bis (phenyl-lower alkyl)-amino, and halo-lower alkyl, e.g. trifluoromethyl), $C_3$-$C_{10}$-cycloalkyl, lower alkoxy, for example methoxy, aryl-lower alkoxy, e.g. phenyl-lower alkoxy, lower alkanoyloxy, N,N-di-lower alkylamino, N-phenyl-lower alkylamino, N,N-bis(phenyl-lower alkyl)-amino, di-lower alkylamino, unsubstituted or lower alkyl substituted and/or mono- or di-oxosubstituted heterocyclylenyl or heterocyclyl, e.g. imidazolidin-2,4-dionenyl or imidazolidin-2,4-dionyl; unsubstituted or substituted aryl, unsubstituted or substituted heterocyclyl, alkylsulfonyl, sulfonylalkyl, unsubstituted, N-mono- or N,N-disubstituted or unsubstituted aminosulfonyl alkyl, hydroxy, mercapto, nitro, halogen, cyano, carboxamido, N-mono- or N,N-disubstituted carboxamido, unsubstituted or substituted alkoxycarbonyl, unsubstituted or substituted alkoxy, formyl or other alkanoyl, unsubstituted or substituted alkenyl or unsubstituted or substituted alkynyl; unsubstituted or substituted aryl selected from phenyl, naphthyl, indenyl, azulenyl and anthryl, preferably unsubstituted or substituted by one or up to three moieties independently selected from those mentioned above as substituents for substituted alkyl;

unsubstituted or substituted heterocyclyl selected from the group consisting of unsubstituted or oxo- and/or lower alkyl-substituted imidazolidinyl, thienyl, oxazolidonyl or thienyl, such as imidazolidin-2,4-dionyl thienyl, 5H-oxazol-2-on-4-yl, 2-methyl-4H-oxazol-4-on-5-diyl, pyrrolidinyl, such as pyrrolidin-1-yl, and triazolyl, such as 1,2,4-triazolyl;

lower alkylsulfonyl; sulfonyl-lower alkyl; unsubstituted, N-mono- or N,N-di-lower alkyl substituted aminosulfonyl alkyl; hydroxy; mercapto; nitro; halogen; cyano; carboxamido; N-mono- or N,N-disubstituted carboxamido, wherein the substitutents are independently selected from lower alkyl and phenyl-lower alkyl; unsubstituted or substituted alkoxycarbonyl where the substituents are independently selected from lower alkyl and phenyl-lower alkyl; unsubstituted or substituted alkoxy wherein the substitutents are independently selected from lower alkyl or phenyl-lower alkyl; formyl or other lower alkanoyl; unsubstituted or lower-alkyl substituted lower alkenyl; or unsubstituted or phenyl-lower alkoxy-substituted lower alkynyl;

R2 is hydrogen or unsubstituted or substituted alkyl with substituents as defined for substituted lower alkyl R1, preferably phenyl-lower alkyl or lower alkyl; unsubstituted or substituted lower alkoxycarbonyl wherein the substituents are independently selected from lower alkyl and phenyl-lower alkyl; unsubstituted or substituted arylsulfonyl, unsubstituted or substituted alkylsulfonyl, especially loweralkyl-phenylsulfonyl or lower alkylsulfonyl; unsubstituted or substituted aryl wherein aryl and the substitutents are defined as under R1, preferably phenyl; carbamoyl or N-mono- or N,N-disubstituted carbamoyl as defined above for R2; silyl substituted by three moieties independently selected from unsubstituted or substituted lower alkyl as defined for unsubstituted or substituted lower alkyl R1 and from substituted or unsubstituted aryl as defined above for R1, or acyl selected from lower alkoxycarbonyl, unsubstituted or substituted aryloxycarbonyl or unsubstituted or substituted aryl-lower alkoxycarbonyl, each with unsubstituted or substituted aryl as defined above for R1, or preferably aryl-carbonyl, aryl-lower alkylcarbonyl or (unsubstituted or substituted lower alkyl)-carbonyl wherein aryl, alkyl and the substituents if present are preferably as defined above; especially lower alkanoyl, and R' is unsubstituted or substituted alkyl;

and in formula II R3 and R4 is lower alkyl or R3 and R4 together form a lower alkylene bridge.

In the above compounds I to XI, each $R_1$ preferably is, where present, independently of the other substituents $R_1$, lower alkyl;

lower alkyl substituted by up to three moieties selected from N,N-di-lower alkylamino, N-phenyl-lower alkylamino, N,N-bis(phenyl-lower alkyl)-amino, N,N-di-lower acylamino, N-lower acylamino, alkylated and/or acylated hydrazino of the formula $R_{20}R_{21}N$—$N(R_{22})$—wherein $R_{20}$ is alkyl or acyl or substituted alkyl (e.g. benzyl) and $R_{21}$ is hydrogen or $R_{20}$ and $R_{22}$ is hydrogen or acyl;

halo-lower alkyl (e.g. trifluoromethyl);

$C_3$-$C_{10}$-cycloalkyl;

lower alkoxy, for example methoxy;

aryl-lower alkoxy, e.g. phenyl-lower alkoxy;

lower alkanoyloxy;

N,N-di-lower alkylamino;

N-phenyl-lower alkylamino, N,N-bis(phenyl-lower alkyl)-amino, N'-phenyl-lower alkylhydrazino, N',N'-bis(phenyl-lower alkyl)-hydrazino, each of which contains phenyl unsubstituted or substituted, preferably unsubstituted;

N',N'-di-lower alkylhydrazino;

unsubstituted or substituted aryl; unsubstituted or substituted heterocyclyl; unsubstituted or lower alkyl substituted and/or mono- or di-oxosubstituted heterocyclenyl or heterocyclyl, e.g. imidazolidin-2,4-dionenyl or imidazolidin-2,4-dionyl or thienyl;

alkylsulfonyl;

sulfonyl alkyl such as lower alkylsulfonylmethyl;

unsubstituted, N-mono- or N,N-disubstituted aminosulfonyl alkyl such as pyrrolidin-1-yl-sulfonylmethyl, di-lower alkylaminosulfonylmethyl, mono-lower alkylaminosulfonylmethyl;

hydroxy;

mercapto;

nitro;

halogen;

cyano;

carboxamido or carboxhydrazido;

N-mono- or N,N-disubstituted carboxamido;

unsubstituted or substituted alkoxycarbonyl;

unsubstituted or substituted alkoxy;

formyl or other alkanoyl;

unsubstituted or substituted alkenyl
or unsubstituted or substituted alkynyl;

unsubstituted or substituted phenyl, preferably unsubstituted or substituted by one, two or three moieties independently selected from those mentioned above as substituents for substituted alkyl;

or $R_1$ is a residue of a boronic acid or an ester thereof.

More preferred meanings of $R_1$ include
unsubstituted or substituted heterocyclyl selected from the group consisting of unsubstituted or oxo- and/or lower alkyl-substituted imidazolidinyl;

thienyl;

oxazolidonyl; such as imidazolidin-2,4-dionyl thienyl, 5H-oxazol-2-on-4-yl, 2-methyl-4H-oxazolin-5-on-4-diyl;

pyrrolidinyl, such as pyrrolidin-1-yl, and triazolyl, such as 1,2,4-triazol-1-yl;

lower alkylsulfonyl;

sulfonyl-lower alkyl;

unsubstituted, N-mono- or N,N-di-lower alkyl substituted aminosulfonyl alkyl;

hydroxy;

mercapto;

nitro;

halogen;

cyano;

carboxamido or carboxhydrazido;

N-mono- or N,N-disubstituted carboxamido, wherein the substitutents are independently selected from lower alkyl and phenyl-lower alkyl;

unsubstituted or substituted alkoxycarbonyl where the substituents are independently selected from lower alkyl and phenyl-lower alkyl;

unsubstituted or substituted alkoxy wherein the substitutents are independently selected from lower alkyl or phenyl-lower alkyl;

formyl or other lower alkanoyl;

unsubstituted or lower-alkyl substituted lower alkenyl;

or unsubstituted or phenyl-lower alkoxy-substituted lower alkynyl;

or $R_1$ is a residue of a boronic acid or an ester thereof.

Of special technical importance are $R_1$ as halogen, cyano or nitro, e.g. chloro, bromo, iodo, cyano, nitro, especially standing in para-position to the indole nitrogen. In the most preferred compounds, n is 1.

R3 and R4 usually are, independently of each other, unsubstituted or substituted alkyl, especially lower alkyl or phenyl lower alkyl, or together form an unsubstituted or substituted alkylene bridge, especially an unsubstituted or lower alkyl substituted lower alkylene bridge (thus forming a ring with the binding nitrogen).

Where R3 and R4 together form an un-substituted or substituted alkylene bridge (thus forming a ring with the binding nitrogen), the alkylene bridge preferably has 2 to 10, more preferably 3 to 6 carbon atoms, thus forming an 3 to 11 or, in the second case, 4 to 7-membered ring with the nitrogen to which they are bound, such as pyrrolidinyl; if substituents are present, they are preferably selected from those mentioned above under "substituted", more preferably from lower alkyl, such as methyl, lower alkoxy, such as methoxy, or hydroxy. Where a phenyl or $C_3$-$C_8$-cycloalkyl ring is condensed to the alkylene bridge at two vicinal carbon atoms, a bicyclic ring is formed bound via ring nitrogen.

R3 and R4 as an alkylene bridge, especially of 3 to 6 carbon atoms, may be interrupted by oxygen or NH.

A preferred method for the synthesis of a compound of the formula I or preferably II uses the above definitions of R1-R4 and n.

Especially preferred is the synthesis of a compound of the formula II, XII and/or XIV (see below), wherein n is 1 or 2, especially 1, $R_1$ is nitro or preferably halogen, especially chlorine, bromine or iodine, and R2, R3 and R4 are as defined above. Of special technical importance in the synthesis of a substituted amide of the formula II (variant (b)) is a compound of formula II and a starting material wherein R1 is nitro, cyano, a residue of a boronic acid or ester thereof or halogen and n is 1 or 2, where halogen is especially chloro, bromo or iodo; especially preferred is n=1 with R1 being in p-position to the oxindole nitrogen.

Where present in the novel compounds of the invention, R1 is often halogen, a residue of a boronic acid or ester thereof, nitro or cyano, preferably cyano or halogen, more preferably wherein n is 1 and $R_1$ is halogen, especially chloro, bromo or iodo; especially preferred is $R_1$ in p-position to the indole nitrogen.

These halogen-containing intermediates are readily available by the described routes.

Novel compounds and/or intermediates of the above formulae I, II, III*, VII, VIII, IX, Xa, Xb, XI, and corresponding salts thereof, are another preferred subject of the invention, e.g.

1) a compound of the formula I, or a salt thereof, wherein n is 1-4, and
each $R_1$ is unsubstituted or substituted alkyl, unsubstituted or substituted aryl, unsubstituted or substituted heterocyclyl, sulfonyl alkyl, N-mono- or N,N-disubstituted or unsubstituted aminosulfonyl alkyl, hydroxy, mercapto, nitro, halogen, cyano, carboxamido, N-mono- or N,N-disubstituted carboxamido, carboxhydrazido, unsubstituted or substituted alkoxycarbonyl, unsubstituted or substituted alkoxy, formyl or other alkanoyl, unsubstituted or substituted alkenyl, unsubstituted or substituted alkynyl, unsubstituted or substituted cycloalkyl, alkanoyloxy, N-mono- or N,N-disubstituted or unsubstituted amino, unsubstituted or substituted hydrazino, or is a residue of a boronic acid or an ester thereof;
provided that when n is 1 and $R_1$ is lower alkyl, $R_1$ is located in the position para to the isatine nitrogen (5-position),
e.g. a compound as above with the exception of a compound of the formula I wherein n is one and $R_1$ is lower alkyl;
and with the further exception of a compound of the formula I wherein $R_1$ is 5- or 7-chloro or 5- or 7-hydroxy or alkoxy or alkanoyloxy, and with further exception of the compound 3-hydroxy-3-butyloxycarbonylmethyl-7-ethyl-6-hydroxy-indolidin-2-one.
Preferred compounds of the formula I, or salts thereof, are those wherein n is 1 or 2, and each $R_1$ independently is bromo or iodo or nitro or cyano or hydroxy or a residue of a boronic acid or an ester thereof.
2) A compound of the formula II as defined above, or a salt thereof, e.g. wherein each $R_1$ independently is halogen or cyano or hydroxy or a residue of a boronic acid or an ester thereof, preferably wherein R1 is halogen, more preferably wherein n is 1 and R1 is halogen, especially chloro, bromo or iodo, especially in p-position to the indole nitrogen;
3) a compound of the formula III* as mentioned above, wherein n, R1 and R2 have the meanings given for compounds of the formula I or II initially described, except for a compound of formula I wherein n is zero or 1 and R1 is lower alkyl;
4) a compound of the formula Xa as defined above, preferably wherein R1 is halogen, cyano, more preferably wherein n is 1 and R1 is halogen, especially chloro, bromo or iodo, especially in p-position to the indole nitrogen;
5) a compound of the formula Xb as defined above, preferably wherein R1 is nitro or cyano or a residue of a boronic acid or an ester thereof, or halogen, such as bromo, chloro or iodo, more preferably wherein n is 1 and R1 is in p-position to the indole nitrogen;
6) a compound of the formula XI, wherein n, R1 and R2 are as initially defined above, and where preferably R1 is nitro or cyano or a residue of a boronic acid or an ester thereof or halogen, especially chloro, bromo or iodo, more preferably wherein n is 1, especially wherein R1 is in p-position to the oxindole nitrogen.

Also preferred is a compound of the formula IX as defined above.

Especially preferred are compounds of the formula II, III*, VII, VIII, Xa, Xb, XI and corresponding salts thereof. Where present, $R_1$ is often halogen, nitro or cyano, preferably halogen; preferably with n being 1, especially preferred is $R_1$ in p-position to the indole nitrogen. Of special technical importance is R1 as halogen, especially chloro, bromo or iodo.

These compounds (most of which are novel) are suitable for further functionalization, e.g. Suzuki-coupling, Sonogashira coupling, Kumada coupling, cyanation, Heck coupling or alkoxy-carbonylation. Most of these products again are novel compounds, which can be further converted into derivatives of I.

Thus, it has been found that some of the above compounds, especially of the formula II, may be further reacted as described below. These are compounds wherein
n, $R_2$, $R_3$ and $R_4$ are as defined above and, where present in case that n is not zero,
each $R_1$ is, independently, unsubstituted or substituted alkyl, unsubstituted or substituted aryl, unsubstituted or substituted heterocyclyl, alkylsulfonyl, sulfonyl alkyl, N-mono- or N,N-disubstituted or unsubstituted aminosulfonyl alkyl, hydroxy, mercapto, nitro, halogen, cyano, carboxamido, N-mono- or N,N-disubstituted carboxamido, unsubstituted or substituted alkoxycarbonyl, unsubstituted or substituted alkoxy, formyl or other alkanoyl, unsubstituted or substituted alkenyl, unsubstituted or substituted alkynyl, unsubstituted or substituted cycloalkyl, alkanoyloxy, N-mono- or N,N-disubstituted or unsubstituted amino, or is a residue of a boronic acid or an ester thereof (educt compounds, e.g. of the formula I or especially II).

In the below compounds XII to $XX^7$, each $R_1$ preferably is, independently of any other substituent $R_1$ if present,
lower alkyl;
lower alkyl substituted by up to three moieties selected from N,N-di-lower alkylamino, N-phenyl-lower alkylamino, N,N-bis(phenyl-lower alkyl)-amino, N,N-di-lower acylamino, N-lower acylamino;
halo-lower alkyl (e.g. trifluoromethyl);
$C_3$-$C_{10}$-cycloalkyl;
lower alkoxy, for example methoxy;
aryl-lower alkoxy, e.g. phenyl-lower alkoxy;
lower alkanoyloxy;
N,N-di-lower alkylamino;
N-phenyl-lower alkylamino, N,N-bis(phenyl-lower alkyl)-amino, each of which contains phenyl unsubstituted or substituted, preferably unsubstituted;
unsubstituted or substituted aryl;
unsubstituted or substituted heterocyclyl; unsubstituted or lower alkyl substituted and/or mono- or di-oxosubstituted heterocyclenyl or heterocyclyl, e.g. imidazolidin-2,4-dionenyl or imidazolidin-2,4-dionyl or thienyl;
alkylsulfonyl;
sulfonyl alkyl such as lower alkylsulfonylmethyl;
unsubstituted, N-mono- or N,N-disubstituted aminosulfonyl alkyl such as pyrrolidin-1-yl-sulfonylmethyl, di-lower alkylaminosulfonylmethyl, mono-lower alkylaminosulfonylmethyl;
hydroxy;
mercapto;
nitro;
halogen;
cyano;
carboxamido;
N-mono- or N,N-disubstituted carboxamido;
unsubstituted or substituted alkoxycarbonyl;
unsubstituted or substituted alkoxy;
formyl or other alkanoyl;
unsubstituted or substituted alkenyl
or unsubstituted or substituted alkynyl;
unsubstituted or substituted phenyl, preferably unsubstituted or substituted by one, two or three moieties independently selected from those mentioned above as substituents for substituted alkyl;
or $R_1$ is a residue of a boronic acid or an ester thereof.
More preferred meanings of R1 in these compounds include
unsubstituted or substituted heterocyclyl selected from the group consisting of unsubstituted or oxo- and/or lower alkyl-substituted imidazolidinyl;

thienyl;
oxazolidonyl; such as imidazolidin-2,4-dionyl thienyl, 5H-oxazol-2-on-4-yl, 2-methyl-4H-oxazolin-5-on-4-diyl;
pyrrolidinyl, such as pyrrolidin-1-yl, and triazolyl, such as 1,2,4-triazol-1-yl;
lower alkylsulfonyl;
sulfonyl-lower alkyl;
unsubstituted, N-mono- or N,N-di-lower alkyl substituted aminosulfonyl alkyl;
hydroxy;
mercapto;
nitro;
halogen;
cyano;
carboxamido;
N-mono- or N,N-disubstituted carboxamido, wherein the substitutents are independently selected from lower alkyl and phenyl-lower alkyl;
unsubstituted or substituted alkoxycarbonyl where the substituents are independently selected from lower alkyl and phenyl-lower alkyl;
unsubstituted or substituted alkoxy wherein the substitutents are independently selected from lower alkyl or phenyl-lower alkyl;
formyl or other lower alkanoyl;
unsubstituted or lower-alkyl substituted lower alkenyl;
or unsubstituted or phenyl-lower alkoxy-substituted lower alkynyl;
or $R_1$ is a residue of a boronic acid or an ester thereof.

Especially preferred is the synthesis of a compound of the formula XII and/or XIV (see below), wherein n is 1 or 2, especially 1, $R_1$ is nitro or preferably halogen, especially chlorine, bromine or iodine, and R2, R3 and R4 are as defined above. Of special technical importance in the synthesis of a substituted amide of the formula II (variant (b)) is a compound of formula II as a starting material wherein R1 is nitro, cyano, a residue of a boronic acid or ester thereof or halogen and n is 1 or 2, where halogen is especially chloro, bromo or iodo; especially preferred is n=1 with R1 being in p-position to the oxindole nitrogen.

Thus, in another embodiment of the invention, a compound of the formula II wherein n, and R2 are as defined for educts as above; and R3 and R4 are, independently of each other, as defined under formula II, preferably are unsubstituted or substituted alkyl or together form an unsubstituted or substituted alkylene bridge (thus forming a ring with the binding nitrogen), is reduced to a corresponding indole derivative in the presence of complex hydrides, preferably borane or borane derivatives.

In one preferred variant of this process, an educt compound of the formula II as just defined is reduced in the presence of a borane di-lower alkyl sulfide (especially borane dimethyl sulfide) to give the corresponding compound of the formula XII:

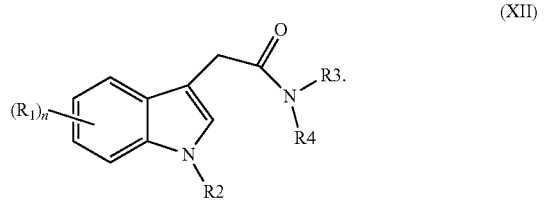

(XII)

Surprisingly, here it is possible to retain the "dangling" amide functionality.

In an alternative variant, reaction of an educt compound of the formula II as just defined in the presence of an alkali metal borohydride in the presence of an boron trifluoride etherate yields a mixture of at least the following three compounds of the formulae XIIIa, XIIIb and XIIIc,

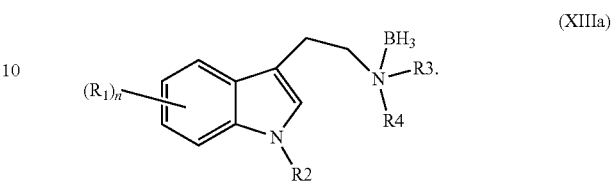

(XIIIa)

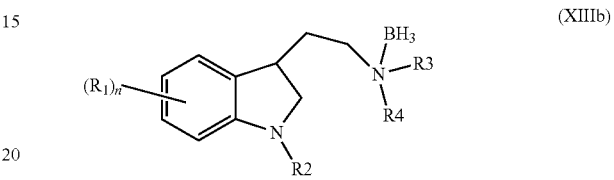

(XIIIb)

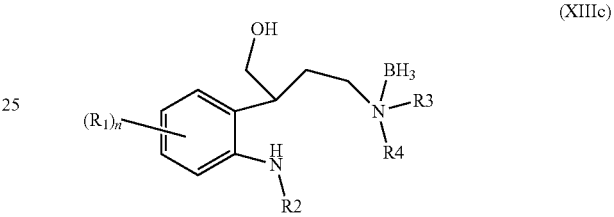

(XIIIc)

wherein n, $R_1$, R2, R3 and R4 are as just defined for the starting compounds of the formula II. Surprisingly, it is possible to convert this mixture into a pure compound of the formula XIV

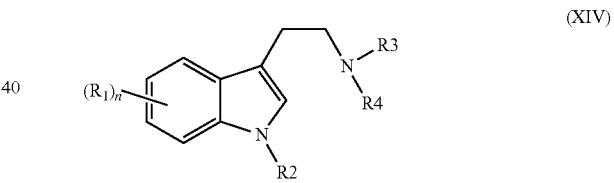

(XIV)

wherein n, $R_1$, R2, R3 and R4 are as defined under formula XIIIa, XIIIb and XIIIc, which forms a further embodiment of the invention.

This can be accomplished by the reaction of a mixture of (XIIIa), XIIIb), and (XIIIc) with diazabicyclo[2.2.2]octane (DABCO) and subsequent dehydrogenation or oxidation with an oxidant. The reaction sequence from the starting material of the formula II to the product of the formula XIV can take place without the need to isolate any of the intermediates, e.g. in one reaction vessel.

In addition, for the intermediate compounds of the formulae I, II, VI, VII to XIV, conversion of functional groups may be made. These also form embodiments of the invention.

For example, in a compound of the formula XIV or XII, where R2 is hydrogen and the other moieties are as defined under these formulae, a moiety R2 other than hydrogen, that is unsubstituted or substituted alkyl, unsubstituted or substituted alkoxycarbonyl, unsubstituted or substituted arylsulfonyl, unsubstituted or substituted alkylsulfonyl, unsubstituted or substituted aryl, carbamoyl, N-mono- or N,N-disubstituted carbamoyl, silyl substituted by three moieties independently selected from unsubstituted or substituted alkyl and substituted or unsubstituted aryl, or acyl may be introduced by standard reactions. Especially, unsubstituted or substituted alkyl is introduced by reaction with a strong base, e.g. NaH, with a corresponding unsubstituted or substituted alkyl derivative of the formula XV, Alk-L    (XV)

wherein Alk is unsubstituted or substituted alkyl, for example benzyl, or unsubstituted or substituted alkoxycarbonyl, unsubstituted or substituted aryl, carbamoyl, N-mono- or N,N-disubstituted carbamoyl, and L is a leaving group, especially halogen, to give the corresponding compound of the formula XII or XIV wherein R2 is unsubstituted or substituted alkyl, while acyl is introduced by reaction with the corresponding acylhalogenides or mixed or symmetric acid anhydrides with one or two of the corresponding acyl moieties, while the silyl derivatives are introduced using the corresponding silyihalogenides, e.g. silylchlorides, under standard reaction conditions, respectively.

In a compound of the formula II where n is zero and the other substituents are as defined above, halogen $R_1$ can be introduced resulting from substitution reaction with an electrophile, especially halogen $R_1$ by reaction with halo-succinimides, or nitro by reaction with nitric acid, optionally in the presence of a strong dehydrating acid, e.g. sulfuric acid, leading to a compound of the formula XVI,

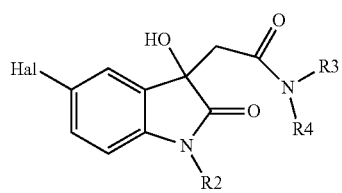

(XVI)

wherein Hal is a moiety resulting from electrophilic substitution, especially nitro or halogen, and R2, R3 and R4 have the meanings given for a compound of the formula II.

Thus, for example, halogenated compounds of this type (R1=halogen) with the formulae XII or XIV can be converted into the corresponding compounds wherein R1 is unsubstituted or substituted aryl by reaction with a compound of the formula (A), Ar—BY$_2$    (A)

wherein Ar is unsubstituted or substituted aryl and Y is OH, into the corresponding compounds of the formulae II$^1$, XII$^1$ or XIV$^1$, respectively,

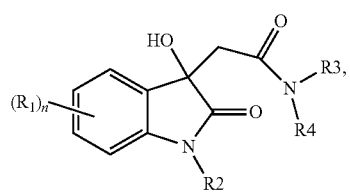

(II$^1$)

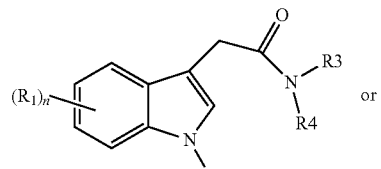

(XII$^1$)

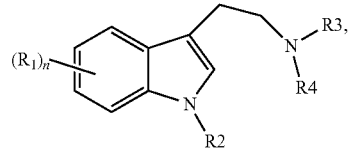

(XIV$^1$)

wherein n is 1 or 2, preferably 1, $R_1$ is unsubstituted or substituted aryl and R2, R3 and R4 have the meanings given under formula (II) by reaction under the conditions of the Suzuki coupling or analogous conditions, i.e. by reaction in the presence of a base (especially an alkalimetal carbonate, such as sodium or caesium carbonate, an alkalimetal alcoholate, such as sodium ethanolate, an alkalimetal hydroxide, such as sodium hydroxide, a tertiary nitrogen base, such as a tri-(lower alkyl)amine, e.g. triethylamine, or an alkali metal phosphate, such as sodium or potassium phosphate) and in the presence of an appropriate palladium catalyst, especially allyl tri-isopropyl-phosphino palladium bromide or Palladium acetate in the presence of tri(ortho-tolylphosphine), bis-diphenylphosphino-ferrocenyl-palladium dichloride- or the like, in an appropriate solvent, e.g. in an ether, such as di-lower alkoxy-C$_2$-C$_7$-alkane, e.g. dimethoxyethane, preferably under an inert gas, e.g. argon, and preferably at elevated temperatures, e.g. between 40° C. and reflux temperature, e.g. under reflux.

Thus, the invention provides a process for the manufacture of a compound of the formula II$^1$, XII$^1$ or XIV$^1$, respectively,

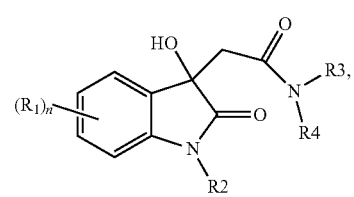

(II$^1$)

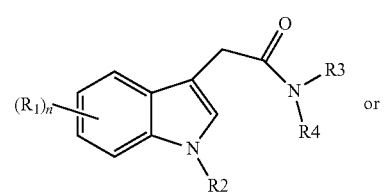

(XII$^1$)

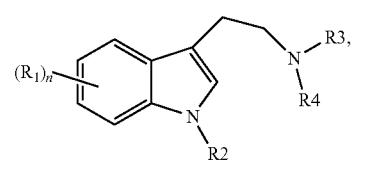

(XIV$^1$)

wherein n is 1 or 2, $R_1$ is unsubstituted or substituted aryl or unsubstituted or substituted heterocyclyl, especially unsaturated heterocyclyl (=heteroaryl) and R2, R3 and R4 have the meanings given under formula II, comprising reacting a compound of the formula II (for the synthesis of compound II¹), XII (for the synthesis of compound XII¹) or XIV (for the synthesis of compound XIV¹) wherein in each case n is 1 or 2, preferably one with the result that then also in the resulting compound n is 1) and R1 is halogen, preferably chloro, bromo or iodo, preferably in para-position to the indole nitrogen, under the conditions of the Suzuki coupling or analogous conditions with a compound of the formula (A),

wherein Ar is unsubstituted or substituted aryl or heterocyclyl and Y is OH, into the corresponding compounds of the formulae II¹, XII¹ or XIV¹, respectively.

Alternatively, halogenated compounds of this type with the formulae II, XII or XIV (wherein $R_1$ is halogen) can be converted into the corresponding compounds wherein R1 is unsubstituted or substituted alkyn-2-yl by reaction with a compound of the formula (B),

wherein Z is unsubstituted or substituted (especially lower) alkyl, preferably aryl-lower alkoxymethyl, preferably benzyloxymethyl, to yield the corresponding compounds of the formulae II², XII² or XIV², respectively,

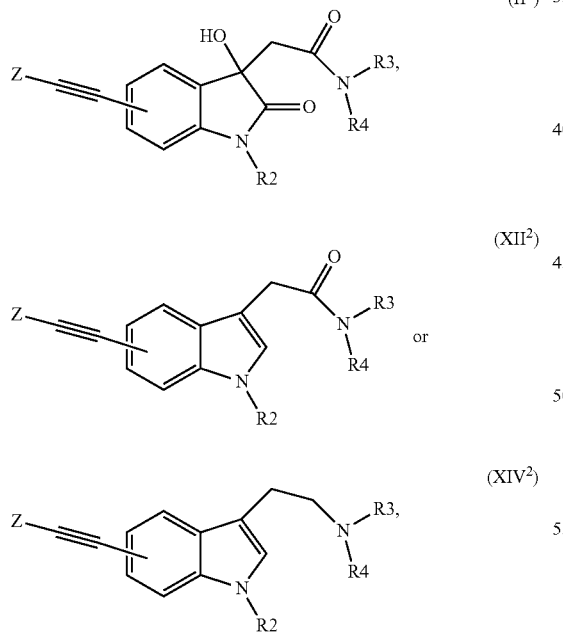

wherein Z is as just defined and R2, R3 and R4 are as defined under formula (II), respectively. The reaction (a Sonogashira coupling) preferably takes place in the presence of CuI, a palladium catalyst, especially Pd(PhCN)$_2$Cl$_2$, a nitrogen base, e.g. piperidine, and a tertiary phosphine, especially a tri-(lower alkyl) phosphine, such as tri-(tert-butyl)phosphine, and in the presence of optional further solvents, such as lower alkanes, e.g. hexanes. The reaction preferably takes place at elevated temperatures, e.g. between 30° C. and reflux temperature, for example at 40 to 60° C.

As a third alternative, halogenated compounds of this type with the formulae II, XII or XIV can be converted into the corresponding compounds wherein R1 is unsubstituted or substituted alken-2-yl by reaction with a compound of the formula (C),

wherein Z* is unsubstituted or substituted (especially lower) alkyl, unsubstituted or substituted aryl, unsubstituted or substituted arylsulfonyl, unsubstituted or substituted alkylsulfonyl, (Y)$_2$N-sulfonyl wherein each Y, independently of the other, is hydrogen or unsubstituted or substituted alkyl, especially lower alkyl or preferably hydrogen, cyano, alkoxycarbonyl, preferably lower alkoxycarbonyl, e.g. methoxycarbonyl or ethoxycarbonyl, or unsubstituted or substituted heterocyclyl (especially heteroaryl, that is, unsaturated heterocyclyl) under conditions of the Heck reaction, that is in the presence of a palladium catalyst, such as Pd (OAc)$_2$, PdCl$_2$, Pd(PPh$_3$)$_4$, Pd$_2$(dba)$_3$ or the like and in the presence of a base, e.g. a tertiary nitrogen base, such as a tri-(lower alkyl)amine, e.g. triethylamine, an alkalimetal carbonate, such as potassium carbonate, or an alkalimetal alcoholate, e.g. sodium ethanolate, to yield the corresponding compounds of the formulae II³, XVII³ or XIV³, respectively,

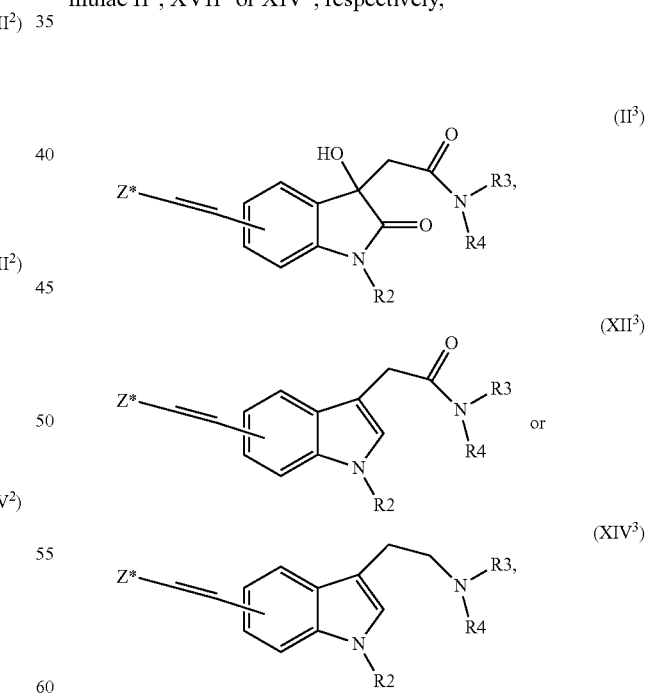

wherein Z* is as just defined and R2, R3 and R4 are as defined for compounds of the formula II.

In a fourth alternative, halogenated compounds of this type of the formulae II, XII and XIV can be converted into the corresponding compounds of the formulae II⁴, XII⁴ or XIV⁴,

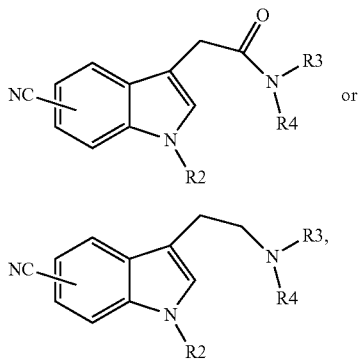

wherein R2, R3 and R4 are as defined above for a compound of the formula II, by reaction with a cyanide salt, especially a zinc cyanide, in the presence of a palladium catalyst, e.g. $Pd_2(dba)_3 \cdot CHCl_3$.

In a fifth alternative, halogenated compounds of this type with the formulae II, XII and XIV can be converted into the corresponding compounds of the formulae $II^5$, $XII^5$ or $XIV^5$,

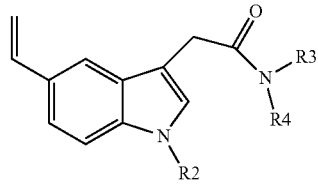

wherein $R_5$ is unsubstituted or substituted alkyl, especially lower alkyl, or unsubstituted or substituted aryl, especially phenyl, and R2, R3 and R4 are as defined above for a compound of the formula II, by reaction with CO in the presence of the corresponding alcohol $R_5$—OH wherein $R_5$ is as described above; the reaction preferably takes place in the presence of a Palladium catalyst, especially $Pd(dppp)Cl_2$ and a tertiary nitrogen base, e.g. a tri-lower alkylamine, such as triethylamine, preferably in a polar solvent, e.g. an alcohol, such as ethanol, and in the presence of carbon monoxide at elevated pressure, e.g. between 10 and 50 bar, preferably at elevated temperatures, e.g. from 40 to 150° C., for example between 100 and 130° C., and preferably in a pressure vessel.

In a sixth alternative, halogenated compounds of this type with the formulae XIV where R1 is halogen can be converted into the corresponding compound of the formulae $XX^6$,

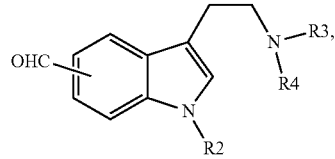

wherein R2, R3 and R4 are as defined above for a compound of the formula II, by reaction with first a lithium alkyl compound to form the lithium derivative and then with DMF or triethyl formate, to obtain ($XX^6$) after hydrolysis. This intermediate offers further possibilities for the synthesis of further tryptamine derivatives, for example as described for compounds of the formula, e.g. by Grignard reactions or other reactions with the aldehyde function.

In these reactions, halogenated compounds of formulae II, XII or XIV are to be understood as those wherein $R_1$ is halogen such as Cl, Br, I, especially standing in para position to the indole nitrogen, For example, the compound of the formula $XX^6$ is converted into the corresponding compound of the formula XXI,

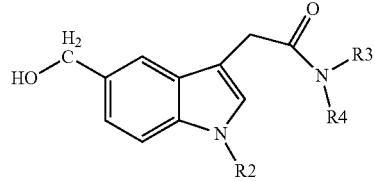

wherein R2, R3 and R4 have the meanings indicated for compounds of the formula $XX^6$, by reaction with a Wittig or Wittig Horner reagent, for example alkyl triaryl phosphonium bromide, e.g. alkyl (e.g. methyl-) triphenyl phosphonium bromide, in the presence of a suitable base, preferably a strong base.

Alternatively, a compound of the formula $XX^6$ is converted into the corresponding hydroxymethyl compound of the formula XXI**,

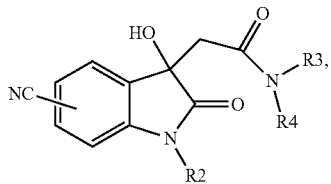

wherein R2, R3 and R4 have the meanings indicated for compounds of the formula $XX^6$, by reduction, for example with a reducing agent such as sodium boro hydride in an alcohol or, lithium aluminium hydride in an ether solvent or especially hydrogenation, in the presence of a selective transition metal catalyst, e.g. a Rhodium complex, such as Rh[DiPFc(COD)]BF$_4$, (see *J. Org. Chem.* 2000, 65, 8933) or a Ruthenium catalyst of the type (cis (PP) Ru trans (dichloro) cis(diamine), see *Angew. Chem. Int. Ed.* 1998, 37, 1703) at elevated pressure, e.g. between 2 and 300 bar, in a polar solvent, e.g. an alcohol, for example methanol or ethanol, at temperatures e.g. from 0 to 60° C., for example at room temperature.

In a seventh alternative, halogenated compounds of this type of the formulae XIV where R1 is halogen, can be converted into the corresponding corn pond of the formula (XX$^7$),

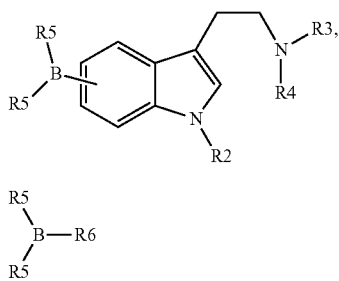

wherein R2, R3 and R4 are as defined above for a compound of the formula II, by reaction with first a lithium alkyl compound to form the lithio derivative and then with an ester of boric acid B, to obtain (XX$^7$), where R5 and R6 are a radical of an alcohol, e.g. lower alkoxy, or together are C$_2$-C$_8$alkylene-dioxy; preferred R5 independently are a residue of a sterically hindered alcohol such as isopropoxy or pinakolyl, and R6 is isopropoxy Depending on the conditions at the work-up, also the boronic acid (R5=OH) may be obtained.

Novel compounds and/or intermediates of the above formulae XII, XIIIa, XIV, XVI, XII$^1$, XIV$^1$, II$^2$, XII$^2$, XIV$^2$, II$^3$, XII$^3$, XIV$^3$, II$^4$, XII$^4$, XIV$^4$, II$^5$, XII$^5$, XIV$^5$, XX$^6$, XXI* and XXI** and corresponding salts thereof are another preferred subject of the invention, e.g.

7) a compound of the formula XII

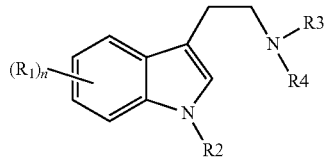

wherein n, R$_1$, R2, R3 and R4 are as defined for the educt compound of formula II, provided that R$_1$ is not 5-methoxy (i.e. methoxy in position para to the indole nitrogen) if n is 1; examples are compounds of the above formula XII wherein R$_1$ is not methoxy if n is 1. Preferred compounds of the formula XII are those wherein R1 is nitro or cyano or a residue of a boronic acid or an ester thereof, or is halogen, especially chloro, bromo or iodo, more preferably wherein n is 1, especially in para-position to the indole nitrogen;

8) a compound of the formula XIIIa as defined above, preferably wherein R1 is nitro or cyano or a residue of a boronic acid or ester thereof or is halogen, especially iodo in paraposition to the indole nitrogen and n is 1;

9) a compound of the formula XIV

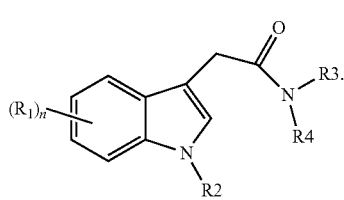

wherein n, R2, R3 and R4 are as defined above and R$_1$ is a residue of a boronic acid or ester thereof, lower alkyl, lower alkyl substituted by up to three moieties selected from N,N-di-lower acylamino and N-lower acylamino, C$_3$-C$_{10}$-cycloalkyl, C$_2$-C$_4$alkoxy, nitro, halogen, lower alkanoyloxy such as C$_1$-C$_4$alkanoyloxy, unsubstituted or substituted aryl (e.g. phenyl), unsubstituted or lower alkyl substituted and/or mono- or di-oxosubstituted nitrogen-heterocyclenyl or nitrogen-heterocyclyl such as imidazolidin-2,4-dionenyl or imidazolidin-2,4-dionyl, sulfonyl alkyl such as lower alkylsulfonylmethyl, mercapto, C$_2$-C$_8$alkanoyl, unsubstituted or substituted alkenyl, or unsubstituted or substituted alkynyl, or a salt thereof; preferably wherein R1 is a residue of a boronic acid or ester thereof, C$_3$-C$_{10}$-cycloalkyl, unsubstituted or substituted phenyl, unsubstituted or substituted alkenyl, unsubstituted or substituted alkynyl. Of special technical interest is a compound of the formula XIV wherein R$_1$ is nitro or halogen, more preferably wherein n is 1 and R1 is nitro or iodo, especially in p-position to the indole nitrogen, or a salt thereof;

10) a compound of the formula II$^1$, XII$^1$ or XIV$^1$ as defined above, or a salt thereof;

11) a compound of the formula II$^2$, XII$^2$ or XIV$^2$, as defined above, or a salt thereof, 12) a compound of the formula II$^3$, XII$^3$ or XIV$^3$ as defined above, or a salt thereof, 13) a compound of the formula II$^4$ or XII$^4$ as defined above, or a salt thereof, 14) a compound of the formula II$^5$ or XII$^5$, as defined above, or a salt thereof, 15) a compound of the formula XIV$^5$, wherein R2, R3, R4 and R$_5$ are as defined above, provided that one of R3 or R4 is not methyl and R3 and R4 together are not phthalyl, or a salt thereof. In a preferred compound of the formula XIV$^5$, R3 and R4 are, independently of each other, C$_2$-C$_4$alkyl or phenylmethyl or phenyl-C$_2$-C$_4$alkyl, whose phenyl rings may be substituted or unsubstituted, or together form an unsubstituted or substituted alkylene bridge of 3 to 6 carbon atoms which may be interrupted by oxygen or NH; if substituents are present, they are preferably selected from those mentioned below under "substituted", more preferably from lower alkyl, such as methyl, lower alkoxy, such as methoxy, or hydroxy.

16) A compound of the formula $XX^6$

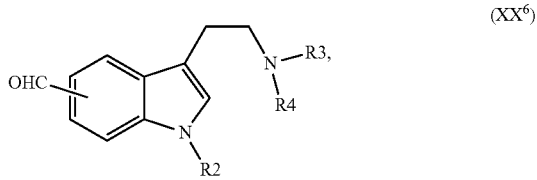

(XX⁶)

wherein R2, R3, R4 and $R_5$ are as defined above, provided that one of R3 or R4 is not methyl and R3 and R4 together are not phthalyl, or a salt thereof. In a preferred compound of the formula $XIV^5$, R3 and R4 are, independently of each other, $C_2$-$C_4$alkyl or phenylmethyl or phenyl-$C_2$-$C_4$alkyl, whose phenyl rings may be substituted or unsubstituted, or together form an unsubstituted or substituted alkylene bridge of 3 to 6 carbon atoms which may be interrupted by oxygen or NH; if substituents are present, they are preferably selected from those mentioned below under "substituted", more preferably from lower alkyl, such as methyl, lower alkoxy, such as methoxy, or hydroxy.

17) A compound of the formula $XX^7$ as defined above, or a salt thereof, 18) a compound of the formula XXI* as defined above, or a salt thereof, 19) a compound of the formula XXI** as defined above, or a salt thereof.

Especially preferred are compounds of the formula XII, XIIIa, XVI, $II^1$, $XII^1$, $XIV^1$, $II^2$, $XII^2$, $XIV^2$, $II^3$, $XII^3$, $II^4$, $XII^4$, $II^5$, $XII^5$, $XIV^5$, $XX^7$, XXI* and XXI** and corresponding salts thereof. Where present, R1 is often halogen, nitro or cyano or a residue of a boronic acid or an ester thereof, preferably halogen; preferably with n being 1, especially preferred is $R_1$ in p-position to the indole nitrogen. Of special technical importance is R1 as halogen, especially chloro, bromo or iodo.

Unless otherwise indicated, the general terms and names used in the description of the present invention preferably have the following meanings (where more specific definitions, in each case separately, or in combination, may be used to replace more general terms in order to define more preferred embodiments of the invention):

Where compounds are mentioned, this means these compounds or salts thereof, e.g., where in the compounds acidic groups are present, salts with bases, such as alkali metal salts or ammonium salts, where basic groups are present, acid addition salts, e.g. with inorganic acids, such chlorides or sulfates, or with organic acids, e.g. sulfonic or carbonic acids, such as methane sulfonates or acetates, where appropriate and expedient. Where both acidic and basic groups are present, also internal salts may be formed.

Preferred salts of the compounds of the invention are acid addition salts such as hydrohalogenides (hydrochlorides), hydrocarbonates, or acylic acid salts like oxalates, fumarates, acetates, citrates and the like.

The term "lower" defines a moiety with up to and including maximally 7, especially up to and including maximally 4, carbon atoms, said moiety being branched or straight-chained. Lower alkyl, for example, is methyl, ethyl, n-propyl, sec-propyl, n-butyl, isobutyl, sec-butyl, tert-butyl, n-pentyl, n-hexyl or n-heptyl.

Halogen or halo is preferably fluoro, chloro, bromo or iodo, most preferably chloro; bromo or iodo (if not stated otherwise).

In "un-substituted or substituted", "substituted", wherever used for a moiety, means that one or more hydrogen atoms in the respective molecule, especially up to 5, more especially up to three, of the hydrogen atoms are replaced by the corresponding number of substituents which preferably are independently selected from the group consisting of alkyl, especially lower alkyl, for example methyl, ethyl or propyl, hydroxy, mercapto, nitro, cyano, halo, halo-lower alkyl, for example trifluoromethyl, $C_6$-$C_{16}$-aryl, especially phenyl or naphthyl (where $C_6$-$C_{16}$-aryl, especially phenyl or napthyl, is unsubstituted or substituted by one or more, especially up to three moieties selected from N,N-di-lower alkylamino, N-phenyl-lower alkyl-amino, N,N-bis(phenyl-lower alkyl)-amino, and halo-lower alkyl, e.g. trifluoromethyl), $C_3$-$C_{10}$ cycloalkyl, lower alkoxy, for example methoxy, aryl-lower alkoxy, e.g. phenyl-lower alkoxy, lower alkanoyloxy, N,N-di-lower alkylamino, N-phenyl-lower alkylamino, N,N-bis(phenyl-lower alkyl)-amino, di-lower alkylamino, unsubstituted or lower alkyl substituted and/or mono- or di-oxosubstituted heterocyclylenyl or heterocyclyl, e.g. unsubstituted or lower alkyl substituted-imidazolidin-2,4-dionenyl or imidazolidin-2,4-dionyl. It goes without saying that substitutents are only at positions where they are chemically possible, the person skilled in the art being able to decide (either experimentally or theoretically) without inappropriate effort which substitutions are possible and which are not.

In unsubstituted or substituted alkyl, alkyl preferably has up to 20, more preferably up to 12 carbon atoms and is linear or branched one or more times; preferred is lower alkyl, especially $C_1$-$C_4$-alkyl. Substituted alkyl is especially lower alkanoyoxy-lower alkyl, such as acetoxymethyl, aryl-lower alkyl, especially benzyl, unsubstituted or mono- or di-oxo-substituted heterocyclylenyl-lower alkyl or heterocyclyl-lower alkyl, hydroxy-lower alkyl, e.g. hydroxy-methyl, mercapto-lower alkyl, e.g. mercaptomethyl, lower alkyl or lower alkyl and oxo substituted heterocyclenyl-lower alkyl, e.g. lower-alkyl-substituted 4H-oxazol-5-on-enyl, or lower alkanoyloxy-lower alkyl, e.g. acetoxymethyl.

In unsubstituted or substituted cycloalkyl, cycloalkyl usually has 3 to 12 carbon atoms; thus, cycloalkyl includes cyclopropyl, cyclobutyl, cyclopentyl, cyclohexyl, cycloheptyl, cyclooctyl, cyclononyl, cyclodecyl, cycloundecyl, cyclododecyl. Substituents, where present, are as defined above for alkyl substituents.

In unsubstituted or substituted aryl, aryl (also in arylene) preferably has a ring system of not more than 24 carbon atoms, especially not more than 16 carbon atoms, is preferably mono-, bi- or tri-cyclic, and is unsubstituted or substituted preferably as defined above under "Substituted"; for example, aryl is selected from phenyl, naphthyl, indenyl, azulenyl and anthryl, and is preferably in each case unsubstituted or substituted phenyl. Aryl, preferably phenyl, is especially preferred.

In unsubstituted or substituted heterocyclyl, heterocyclyl is preferably a heterocyclic radical that is unsaturated, saturated (then heterocyclyl is heteroaryl, that is, if the maximum possible number of double bonds is present in the ring) or partially saturated in the bonding ring and is preferably a monocyclic or in a broader aspect of the invention bicyclic or tricyclic ring; has 3 to 24, more preferably 4 to 16 ring atoms; wherein at least in the ring bonding to the radical of the molecule of formula I one or more, preferably one to four, especially one or two carbon ring atoms are replaced by a heteroatom selected from the group consisting of nitrogen, oxygen and sulfur, the bonding ring preferably having 4 to 12, especially 5 to 7 ring atoms; heteroaryl being unsubstituted or substituted by one or more, especially 1 to 3, substitutents independently selected from the group consisting of the substituents defined above under "Substituted" and/or by one or more oxo groups; especially being a heteroaryl radical selected from the group consisting of imidazolyl, thienyl, furyl, pyranyl, thiopyranyl, benzofuranyl, pyrrolinyl, pyrrolidinyl, imidazolidinyl, benzimidazolyl, pyrazolyl, pyrazinyl, pyrazolidinyl, thiazolyl, oxazolyl, pyridyl, pyrazinyl, pyrimidinyl, piperidyl, piperazinyl, pyridazinyl, morpholinyl, thiomorpholinyl, indolizinyl, isoindolyl, indolyl, benzimidazolyl, indazolyl, triazolyl, isoquinolyl, quinolyl, tetrahydroquinolyl, tetrahydroisoquinolyl, benzofuranyl, dibenzofuranyl, benzothiophenyl, dibenzothiophenyl, naphthyridinyl, quinoxalyl, quinazolinyl, carbazolyl, β-carbolinyl, phenanthridinyl, acridinyl, perimidinyl, phenanthrolinyl, furazanyl, phenazinyl, phenothiazinyl and phenoxazinyl, each of these radicals being unsubstituted or substituted by one to three radicals selected from the group consisting of lower alkyl, especially methyl or tert-butyl, and oxo. Especially preferred are unsubstituted or oxo- and/or lower alkyl-substituted imidazolidinyl, thienyl, oxazolidonyl, triazolyl or pyrrolidinyl such as imidazolidin-2,4-dionyl, thienyl, oxazolon-yl, 2-methyl-4H-oxazol-5-onyl, pyrrolidin-1-yl or 1,2,4-triazolyl.

In unsubstituted or lower alkyl substituted and/or mono- or di-oxosubstituted heterocyclylenyl or heterocyclyl, heterocyclyl is preferably as defined above. Heterocyclylenyl means a heterocyclyl moiety bound to the rest of the molecule by a double bond, while heterocyclyl is bound via a single bond. Preferred are unsubstituted or lower alkyl substituted-4H-oxazol-5-on-enyl, or the moieties mentioned as preferred for unsubstituted or substituted heterocyclyl.

In Alkylsulfonyl, alkyl is preferably as defined above; preferred is lower alkylsulfonyl, such as methanesulfonyl.

In Sulfonyl alkyl, alkyl is preferably as defined above; preferred is sulfonyl-lower alkyl, such as sulfonylmethyl.

In unsubstituted or substituted arylsulfonyl, unsubstituted or substituted aryl is preferably as defined above, e.g. lower-alkyl substituted phenyl; preferred is toluolsulfonyl.

In unsubstituted or substituted alkylsulfonyl, unsubstituted alkyl is preferably as defined above, preferably lower alkyl; preferred is lower alkylsulfonyl, e.g. methanesulfonyl.

In N-mono- or N,N-disubstituted or unsubstituted aminosulfonyl alkyl, the substituents are preferably selected from those mentioned above under "substituted", especially aryl or heterocyclyl, such as pyrrolidinyl, while alkyl is preferably as defined above, especially lower alkyl, such as methyl. Aminosulfonyl alkyl is preferably aminosulfonyl lower alkyl, especially aminosulfonylmethyl.

In N-mono- or N,N-disubstituted carboxamido, the substituents if present are preferably selected from unsubstituted or substituted alkyl, especially lower alkyl, such as lower alkyl or phenyl-lower alkyl, e.g. benzyl. For example, carboxamido may stand for a residue —CO—NR$_{23}$R$_{24}$, wherein R$_{23}$ and R$_{24}$ independently are H, lower alkyl, lower alkenyl, lower alkyl or alkenyl substituted by OH or oxo; or R$_{23}$ and R$^{24}$ together form a C$_3$-C$_{11}$alkylene or alkenylene which is unsubstituted or substituted by OH or oxo, especially by 1 or 2 groups =O. Consequently, carboxhydrazido embraces a residue —CO—NH—NR$_{23}$R$_{24}$, wherein R$_{23}$ and R$_{24}$ independently are as defined above.

Hydrazino embraces a residue of the formula R$_{20}$R$_{21}$N—N(R$_{22}$)— wherein R$_{20}$ is alkyl or acyl or substituted alkyl (e.g. benzyl) and R$_{21}$ is hydrogen or R$_{20}$ and R$_{22}$ is hydrogen or acyl.

In unsubstituted or substituted alkoxycarbonyl, the substituents if present are preferably selected from unsubstituted or substituted alkyl, especially lower alkyl, such as lower alkyl or phenyl-lower alkyl, e.g. benzyl.

In unsubstituted or substituted alkoxy, the substituents are preferably selected from alkyl, especially as defined above, preferably lower alkyl, or phenyl-lower alkyl, e.g. benzyl.

Acyl is preferably a linear, branched, cyclic, cyclic-linear, saturated or partially or totally unsaturated organic carboxylic acid radical, especially unsubstituted or substituted alkoxycarbonyl, unsubstituted or substituted aryloxycarbonyl, unsubstituted or substituted aryl-lower alkoxycarbonyl, or preferably aryl-carbonyl, aryl-lower alkylcarbonyl or (unsubstituted or substituted alkyl)-carbonyl wherein aryl, alkyl and the substituents if present are preferably as defined above. Preferred is lower alkanoyl, especially acetyl.

In formyl or other alkanoyl, alkanoyl is preferably lower alkanoyl, such as acetyl.

In unsubstituted or substituted alkenyl, alkenyl is preferably a moiety with up to 20 carbon atoms, preferably lower alkenyl, wherein one or more, especially one, double bonds are present. If substituents are present, they are mainly selected from those given above under "Substituted" where chemically possible, as can be deduced conveniently by the person skilled in the art. In unsubstituted or substituted alkynyl, alkynyl preferably has up to 20 carbon atoms; more preferred is lower alkynyl. If substituents are present, they are mainly selected from those given above under "Substituted" where chemically possible, as can be deduced conveniently by the person skilled in the art. Especially preferred is aryl-lower alkoxy-lower alkynyl, such as 3-benzyloxy-2-propynyl.

In unsubstituted or substituted alkoxycarbonyl, alkoxy is preferably as defined above, especially lower alkoxy, such as methoxy, while the substitutents, if present, are preferably chosen from those mentioned above, especially lower alkyl, or aryl-lower alkyl, such as benzyl. Preferred is tert-butoxycarbonyl or benzyloxycarbonyl.

In N-mono- or N,N-disubstituted carbamoyl, the substituents are preferably selected from those mentioned above under "substituted", more preferably from lower alkyl, and aryl-lower alkyl, such as benzyl.

In silyl substituted by three moieties independently selected from unsubstituted or substituted alkyl and substituted or unsubstituted aryl, "unsubstituted or substituted", "alkyl" and "aryl" preferably have the meanings given above; preferred is tri-(lower alkyl)-silyl, such as trimethylsilyl or tert-butyl-dimethylsilyl.

A tertiary nitrogen base NB where the nitrogen is not part of a ring is preferably a nitrogen substituted by three moieties selected from alkyl, such as lower alky, especially ethyl, C$_3$-C$_7$-cycloalkyl, such as cyclohexyl, or phenyl-lower alkyl, such as benzyl. Preferred as base NB are N,N-dicyclohexyl-N-lower alkylamines, such as dicyclohexyl-ethylamine, or especially tri-lower alkylamines, such as triethylamine.

An active carbonic ester of the formula IV, wherein X is halogen, is especially the corresponding bromide or especially chloride.

Unsubstituted or substituted alkyl for R' is preferably as defined above in general, more preferably selected from lower alkyl or phenyl-lower alkyl, such as methyl, ethyl or benzyl.

An active amido carbonic acid derivative of the formula V, wherein X is halogen, is preferably the chloride.

The reactions presented above and below in general terms are conducted under standard conditions for the person skilled in the art for corresponding known reactions. In detail, the following reaction conditions are preferred:

Reaction of a compound of the formula VI with malonic acid in the presence of a pyridine, especially a picoline or most especially pyridine, in an N,N-(di-lower alkyl)-lower alkanoylamide, preferably dimethylformamide (DMF) followed by conversion into the salt of the base NB given in formula III, preferably takes place at temperatures between 30° C. and reflux temperature, e.g. between 50 and 90° C., for example between 60 and 80° C.

Preferably, the reaction of the compound of the formula VI with malonic acid in the presence of a pyridine, and the subsequent conversion into the salt of the formula III with the base NB and reaction a) or b) above take place in the same reaction vessel (one pot synthesis), that is, without isolation of the intermediate product of the formula III.

For the conversion of a compound of the formula II into a compound of the formula VII, the reaction preferably takes place in acetic acid in the presence of an acidic catalyst, preferably an inorganic acid, especially sulphuric acid, phosphoric acid, or hydrogen bromide, preferably at elevated temperatures, e.g. between 50 and 100° C., and in the presence of a small amount of water.

For the transformation of a compound of the formula VII into the corresponding free alcohol of the formula VIII, hydrolysis in the presence of a base and water or trans-esterification in the presence of an alcohol, e.g. a lower alkanol, such as methanol or ethanol, and a base, e.g. an alkali metal salt base, such as an alkali metal carbonate, e.g. sodium or potassium carbonate, or the alkali metal salt of an organic acid, e.g. an alkali metal lower alkanoate, such as sodium acetate, at elevated temperatures, e.g. between 60° C. and the reflux temperature of the reaction mixture, for example between 80° C. and reflux temperature, is preferred. The reaction can also take place without isolation of the compound of the formula VII.

In the reaction of a compound of the formula II wherein R2 has one of the meanings given above with a dehydrating agent, preferably an acid anhydride (preferably an anhydride of a lower alkanoic acid, especially acetic anhydride) to give a compound of the formula Xa, the reaction preferably takes place in this solvent, at elevated temperatures, especially under reflux.

If desired, reduction of the resulting compound of the formula Xa in the presence of a reductant (especially hydrogen in the presence of a catalyst, such as a noble metal catalyst with or without a carrier, e.g. Pd or Pd on charcoal, or hydrogen in statu nascendi, which is generated by a reactive (non-noble) metal, especially zinc) to a compound of the formula Xb then preferably takes place in the presence of an organic acid, especially acetic acid, at elevated temperatures, e.g. between 50° C. and the reflux temperature of the reaction mixture, for example under reflux.

For the alternative embodiment of the invention where a compound of the formula Xa is obtained by hydrogenation of a compound of the 3-hydroxy group in a compound of the formula II, the hydrogenation preferably takes place with hydrogen in the presence of a catalyst, especially a noble metal catalyst with or without carrier, such as Pd or Pd on charcoal, under standard reaction conditions.

The conversion of a compound of the formula Xb to a Spiro indole of the formula XI by reaction with formaldehyde preferably takes place in a lower alcohol such as methanol or ethanol at elevated temperatures, e.g. between 50° C. and reflux temperature.

For the reaction where a compound of the formula II is reduced to a corresponding indole derivative in the presence of complex hydrides, e.g. lithium aluminium hydride (for reaction conditions see J. Org. Chem. 53, 2844 (1988) or J. Med. Chem. 31, 1244 (1988)) or preferably borane or borane derivatives (see e.g. Tetrahedron: Asymmetry 7, 285, 1996) are used, advantageously under borane generation in situ, especially takes place in an appropriate solvent, such as an ether, e.g. a di-lower alkoxy lower alkane, such as dimethoxy ethane, di-ethylenglycol-di-methyl ether or THF, in the case of use of a borohydride derivative, e.g. an alkali metal borohydride, such as sodium borohydride, preferably in the presence of a boron trifluoride complex, e.g. $BF_3$etherate (the complex with diethyl ether), preferably at elevated, ambient or slightly lowered temperatures, e.g. between −30 and +50° C., especially between −30 and 28° C.

In the variant with presence of a borane di-lower alkyl sulfide (especially borane dimethyl sulfide) to give the corresponding compound of the formula XII, the reaction preferably takes place in an appropriate solvent, e.g. an ether, for example a di-lower alkoxy lower alkane, such as dimethoxy ethane, in the presence of a boron trifluoride complex, e.g. $BF_3$etherate, especially at lowered, ambient and/or elevated temperature, preferably temperatures between −10° C. and 80° C.

In the embodiment of the invention where the reaction with an alkali metal borohydride in the presence of an boron trifluoride etherate yields a mixture of three compounds of the formulae XIIIa, XIIIb and XIIIc, the reaction preferably takes place in an appropriate solvent, e.g. the presence of an ether, for example a di-lower alkoxy lower alkane, such as dimethoxy ethane, at preferred temperatures between −20 and 50° C., e.g. between −15 to 30° C., and the subsequent reaction with DABCO (which can preferably follow without isolation of the mentioned product mixture, that is, as one pot reaction, after addition of a metal salt base, e.g. an alkali metal hydroxide in water, such as sodium or potassium hydroxide) at elevated temperatures, e.g. between 50° C. and reflux temperature, for example at about 80° C. After partial isolation from the inorganic phase, preferably with some additional extraction steps, the products are dissolved in an appropriate solvent, e.g. an ether, such as a di-lower alkyl ether, e.g. tert-butyl-methyl-ether, and oxidized with an appropriate oxidant, e.g. as mentioned above, especially manganese dioxide, at preferred temperatures between 10° C. and the reflux temperature, e.g. between 20 and 50° C.

The conversion in a compound of the formula XIV or XII, where R2 is hydrogen and the other moieties are as defined under these formulae, to introduce a moiety R2 other than hydrogen, in the presence of sodium hydride with a corresponding unsubstituted or substituted alkyl derivative of the formula XXI preferably takes place in an appropriate solvent, such as an N,N-di-(lower alkyl)-lower alkanoylamide, e.g. N,N-dimethylformamide, at appropriate temperatures, e.g. between −10 and 40° C., preferably under an inert gas, such as nitrogen.

The reaction for the introduction of a moiety resulting from electrophilic substitution, especially nitro or halogen, especially chloro $R_1$ into a compound of the formula II, takes place under standard conditions for the introduction of such groups, for example by reaction with halo-succinimides, especially N-chloro succinimide leading to the corresponding halogenated compound of the formula XVI, preferably takes place in an appropriate solvent or solvent mixture, e.g. a lower alkanoic acid, e.g. acetic acid, dichloroethane, and/or an aromatic solvent, e.g. chlorobenzene, at customary temperatures, e.g. at temperatures between 20 and 30° C., for the introduction of nitro by reaction with $HNO_3$, optionally in the presence of sulfuric acid or acetic acid.

The reaction of a compound of the formula $XX^6$ into the corresponding compound of the formula XXI preferably takes place in an appropriate solvent, e.g. an ether, such as tetrahydrofurane, preferably under inert gas, e.g. argon or nitrogen, at preferred temperatures from −10° C. to the reflux temperature of the mixture, e.g. from 15 to 40° C., e.g. at room temperature. As strong base, preferably an alkoholate salt is used, e.g. an alkali metal lower alkoxide, such as sodium or potassium tert-butoxide. The invention also relates to the single reaction steps of the reactions mentioned above, as well as combinations of two or more thereof as far as they are consecutive steps in a reaction sequence, as well as novel intermediates.

The formation of compounds of the formula $XX^7$ preferably takes place at lower temperatures, e.g. in the range of about −170° C. to about room temperature, especially between about −100 and 0° C. It is preferably carried out under exclusion of moisture and oxygen, e.g. under inert atmosphere, and in an appropriate solvent such as ether (e.g. diethyl ether). Lithium alkyls usable are those commonly known in the art, e.g. butyllithium. Preferred boron compounds are as initially described. Workup with hydrolysis may be carried out under conditions as commonly known, e.g. ambient conditions.

Where necessary and appropriate, in any of the reactions shown above protecting groups may be introduced and removed at appropriate reaction stages which allow to protect functional groups that are intended not to participate in the respective reaction reversibly. Examples of protection groups, their introduction and their removal are presented in T. W. Greene and P. G. M. Wuts, "Protective Groups in Organic Synthesis", $3^{rd}$ edition, John Wiley & Sons, Inc., New York/Weinheim 1999, which is herewith incorporated by reference in respect to the protection groups, their removal and their introduction, respectively.

Starting materials for which the synthesis is not mentioned in the present disclosure are either commercially available, prepared according to standard methods or known in the art.

Preferred Embodiments of the Invention

The invention relates to the single reaction steps as given above, as well as any combination of two or more reaction sequence steps that are in succession, that is, where the product of one reaction is the precursor of the next reaction that is part of such combination.

Preferred embodiments of the invention can be found in the claims, which are incorporated here by reference, the dependent claims representing preferred embodiments of the invention. In the claims, more general definitions can be replaced with the more specific definitions given above, independently or together with some or all other general expression, thus leading to further preferred embodiments of the invention.

Highly preferred embodiments of the invention are those where in the processes mentioned above the formulae represented above are replaced with the corresponding specific compounds mentioned in the examples.

Very preferred process steps, combinations of process steps, novel starting materials and intermediates (compounds) that are part of the present invention are described in the subsequent examples, thus forming very preferred embodiments of the invention.

EXAMPLES

The following examples serve to illustrate the invention without limiting the scope thereof. Wherever ambient temperature or room temperature is mentioned, this denotes a temperature in the range 20-25° C. unless stated otherwise.

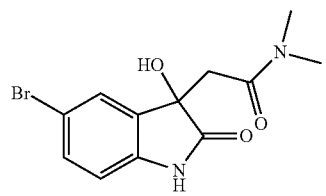 [SMILES: CN(C)C(=O)CC1(O)C(=O)Nc2ccc(Br)cc21]

Example 1

Preparation of 2-(5-Bromo-3-hydroxy-2-oxo-2,3-dihydro-1H-indol-3-yl)-N,N-dimethyl-acetamide A 2 L flask fitted with an inner thermometer, mechanical stirrer, and reflux condenser is charged with 5-bromo-isatin (100 g, 0.442 mol), malonic acid (55.2 g, 053 mol), pyridine (100.6 g, 1.274 mol), dimethyl formamide (80 g), and ethyl acetate (100 g). When the temperature of the mixture reaches 60° C., the bromo isatin starts to dissolve, and a deep red mixture forms. Carbon dioxide starts to evolve, and after about 45 minutes the precipitation of the intermediate pyridinium (5-bromo-3-hydroxy-2-oxo-2,3-dihydro-1H-indol-3-yl)-acetate starts. The reaction mixture is kept at 80° C. for another 3 hours. Then triethyl amine (49.2 g, 0.486 mol) is added, and the pyridinium salt dissolves to give a deep brown solution. This solution is allowed to cool to 50° C., and then a solution of dimethyl carbamoyl chloride (48 g, 0.442 mol, CAUTION: carcinogen) in 40 g of ethyl acetate is added dropwise during 30 minutes. Carbon dioxide evolves, and the temperature rises to 60° C. After about 45 minutes, the product starts to precipitate from the reaction mixture. The mixture is kept at 60° C. for another hour, and then water (500 mL) and 36% HCl (250 mL, 4 mol) are added in that order during 10 minutes. The product is filtered off, and reslurried in an mixture of acetone/water (500 mL, 1:1, v:v). The slurry is filtered again, and the product is finally dried to give the title compound as a gray powder which is of suitable purity for direct use in the further steps. Yield: 75.2 g (54.2%). An analytically pure sample is obtained by recrystallization from methanol, mp=245-246° C., dec. $^1$H-NMR (DMSO-D6, 300 MHz): δ 2.64 (s, 3, CH$_3$), 2.93 (s, 3, CH$_3$), 2.93, 3.27 (AB, 2, $^2$J=16.5 Hz, CH$_2$), 6.01 (br s, 1, OH), 6.73 (d, 1, $^3$J=8.2 Hz, H-7), 7.30 (dd, 1, $^3$J=2.0 Hz, H-6), 7.42 (d, 1, H-4), 10.18 (br s, 1, NH). $^{13}$C-NMR (DMSO-D6, 75 MHz) δ 35.04, 37.45 (N(CH$_3$)$_2$), 40.78 (CH$_2$), 73.90 (C-3), 111.85 (C-7), 113.29 (C-5), 127.03 (C-4), 131.83 (C-6), 135.78 (C-9), 143.18 (C-8), 168.93 (CONMe$_2$), 178.68 (C-2).

Example 2

Preparation of 2-(5-Bromo-1H-indol-3-yl)-N,N-dimethyl-acetamide

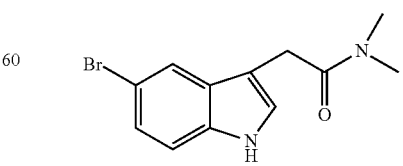

A 1 L flask fitted with an inner thermometer, mechanical stirrer and dropping funnel is charged with 34.8 g of 2-(5- bromo-3-hydroxy-2-oxo-2,3-dihydro-1.H.-indol-3-yl)-.N, N.-dimethyl-acetamide (0.111 mol) and 250 mL of dimethoxy ethane (DME). The obtained suspension is cooled with an ice bath, and then $BF_3$-etherate (28.3 g, 0.2 mol) is added while the inner temperature is maintained at 20° C. This leads to the formation of a solution after a few minutes. The temperature is kept at 20° C., and 12.0 g of 95% borane dimethylsulfide complex (0.15 mol) is added dropwise during 10 minutes. The cooling bath is then removed, and the temperature of the mixture rises slowly, while a gas is formed. When the temperature reaches 48° C., the product starts to precipitate whilst the temperature continues to rise until it reaches 58° C. After about 10 minutes the temperature starts to fall to ambient temperature. After 75 minutes, the reaction mixture is quenched with 100 mL of 4 N NaOH (no exothermic reaction), and then the obtained olive green suspension is heated under reflux for 30 minutes. After cooling to ambient temperature, the mixture is filtered, and most of the DME is removed from the filtrate by rotary evaporation (rotavapor). To the residue, acetone (about 100 mL) is added, and the product is allowed to crystallize at 4° C. for 30 minutes. The crude product is filtered off and washed with little acetone and pentane to give 22.2 g of beige crystals. These are purified by crystallization from methanol/Norite (activated charcoal) (385 mL, 2.2 g) to give 16.2 g of colorless crystals. The residue obtained after removal of the solvent is recrystallized from methanol/Norite (75 mL/1.2 g) to give a second crop of 3.0 g. Combined yield of the title compound (19.2 g, 61.4%), mp=201-202° C. $^1$H-NMR (DMSO-D6, 300 MHz) δ 2.80, 3.00 (2 s, 3H each $N(CH_3)_2$); 3.71 (s, 2H, $CH_2$); 7.15 (dd, 1H, 3J=8.5 Hz, 4J=2 Hz, H-6); 7.25 (d, 1H, J=2.3 Hz, H-2); 7.30 (d, 1H, H-7); 7.73 (d, 1H, H-4); 11.09 (br s, 1H, NH). $^{13}$C-NMR (DMSO-D6, 75 MHz): δ 31.12 ($CH_2$); 35.68, 37.91 ($CH_3$); 108.88, 111.71, 113.99 (CH), 121.98 (CH), 124.09 (CH), 125.97 (CH), 129.93, 135.54, 171.00 (CO).

Example 3

Preparation of [2-(5-Bromo-1H-indol-3-yl)-ethyl]-dimethyl-amine

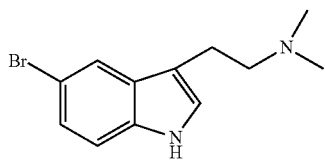

A 1 L flask is charged with 2-(5-bromo-3-hydroxy-2-oxo-2,3-dihydro-1H-indol-3-yl)-N,N-dimethyl-acetamide (Example 1) (31.2 g, 0.1 mol), sodium borohydride (11.8 g 96%, 0.3 mol), and 250 mL of dimethoxyethanol (DME). The mixture is cooled to −15° C., and to the stirred suspension, $BF_3$-etherate (56.6 g, 0.4 mol) is added dropwise. The temperature is maintained between −15 and −10° C. during the exothermic addition. The mixture is then allowed to warm slowly to ambient temperature (25-27° C.), and left stirring over night. The mixture is cooled with an ice bath and quenched by the addition of 4N NaOH (200 mL). The formed viscous emulsion is heated to 80° C. for 30 minutes, then diazabicyclo[2.2.2]cyclooctane (DABCO) (12.7 g 97%, 0.11 mol) is added, and then the mixture is heated for two additional hours under reflux. After cooling to ambient temperature, the aqueous layer is removed and the organic layer is extracted twice with each 50 mL of a 4 N NaOH solution. After re-extraction of the combined inorganic layers with toluene (150 mL), the aqueous phase is disposed off, and the toluene layer is added back into the reaction vessel. To the vessel, additional toluene (150 mL) is added and the mixture is then extracted with water (200 mL). The aqueous layer is separated, and extracted twice with each 150 mL of toluene. After disposal of the inorganic the combined toluene layers are extracted for three times with water (300 mL, 2×150 mL), and the aqueous layer is again discarded. The toluene layer is then extracted twice with 4N HCl (100 mL and 50 mL). During the combined acidic extracts, the pH is then adjusted to 14 by the addition of 4 N NaOH. Then the aqueous layer is extracted twice with tert-butyl methyl ether TBME (150 mL and 50 mL), and the combined extracts are washed with brine (50 mL) and then transferred into a 500 mL flask. To the stirred TBME solution, $MnO_2$ (34.8 g, 0.4 mol) is then added, and temporarily the temperature rises to 40° C. After one hour the aniline by-product has been converted completely, and then the $MnO_2$ is filtered off. Removal of the solvent from the filtrate gives the title product as a colourless viscous oil which crystallizes (23.85 g, 85%), mp=95-96° C. $^1$H-NMR ($CDCl_3$, 300 MHz): δ 2.37 (s, 6H, 2 CH3), 2.27 (m, 2H, $CH_2CH_2NMe_2$), 2.90 (m, 2H, $CH_2CH_2NMe_2$), 6.86 (d, 1H, $^3$J=1.8 Hz, H-2), 7.03 (d, 1H, $^3$J=8.8 Hz, H-7), 7.21 (dd, 1H, $^4$J=1.8 Hz, H-6), 7.70 (d, 1H, H-4), 9.36 (br s, 1H, H-1). $^{13}$C-NMR ($CDCl_3$, 75 MHz) δ 23.60 ($CH_2CH_2NMe_2$), 45.47 ($N(CH_3)_2$), 60.25 ($CH_2CH_2NMe_2$), $\overline{112.42}$ (C-5), 112.98 (C-$\overline{7}$), 113.54 (C-3), $12\overline{1}.39$ (C-4), 123.61 (C-2), 124.64 (C-6), 129.43 (C-8), 135.36 (C-9).

NMR-data of the intermediate side-product 2-(2-amino-5-bromo-phenyl)-4-dimethyl-amino-butan-1-ol, which is formed by ring opening/reduction: $^1$H-NMR ($CDCl_3$, 300 MHz) δ 1.60-1.77, 1.89-2.10 (2 m, 1H each, $CH_2$); 2.23 (s, 6H, $N(CH_3)_2$); 2.24-2.41 (m, 2H, $CH_2NMe_2$); 3.18-3.24 (m, 1H, $CH_2OH$); 3.24-3.34 (m, 1H, CH); 3.64-3.70 (m, 1H, $CH_2OH$); 3.73 (br s, 1H, OH); 6.46 (d, 1H, 3J=8.2 Hz, Ar H-3); 7.08 (dd, 1H, 4J=2 Hz, Ar H-4); 7.14 (1H, Ar H-6). $^{13}$C-NMR ($CDCl_3$, 75 MHz) δ 32.33 ($CH_2$); 40.44 (CH); 45.72 ($N(CH_3)_2$); 53.88 $CH_2NMe_2$); 57.63 ($CH_2OH$); 110.25 (Ar C-1); 110.89 (Ar C-3); 127.05, 130.83 (Ar C-4, C-6); 135.50 (Ar C-5); 150.64 (Ar C-2).

Example 4

Preparation of [2-(1-Benzyl-5-bromo-1H-indol-3-yl)-ethyl]-dimethyl-amine

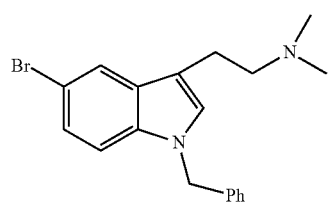 [SMILES: CN(C)CCc1cn(Cc2ccccc2)c2ccc(Br)cc12]

In a 100 mL flask with inner thermometer and stirrer, 3.76 g (14.1 mmol) of [2-(5-bromo-1H.-indol-3-yl)-ethyl]-dimethyl-amine (Example 3) is dissolved in 40 mL of dry N,N-dimethyl formamide (DMF). To the solution NaH (95%, 366 mg, 14.5 mmol) is added under an inert atmosphere. Hydrogen gas is forming, and the NaH dissolves under slight warming during about 30 minutes. The solution is then cooled to 5° C., and a solution of benzyl chloride (1.77 g, 14 mmol) in 10 mL of DMF is added dropwise during a 10 minute period. The cooling bath is removed, and the mixture is left stirring over night at ambient temperature. Then the mixture is diluted with water (about 100 mL) and extracted with n-hexane/ether (about 1:1, 3×100 mL), and the combined organic extracts are re-extracted with water (3×100 mL). After drying and removal of the solvent, the remaining oil is chromatographed on silica (80 g, 230-400 mesh, ethyl acetate/ethanol 5:2+1% NH$_3$) to give 3.86 g (76.6%) of the title product as an oil which crystallized on standing, mp=54-55° C. $^1$H-NMR (CDCl$_3$, 300 MHz): δ 2.33 (s, 6H, N(CH$_3$)$_2$); 2.57-2.65, 2.86-2.94 (2 m, 2H each, CH$_2$CH$_2$); 5.23 (s, 2H, CH$_2$Ph); 6.96 (s, 1H, H-2); 7.05-7.08 (m, 2H, Ph-H) 7.14 (d, 1H, $^3$J=9 Hz, H-7); 7.22 (dd, 1H, $^4$J=2 Hz, H-6); 7.25-7.33 (m, 3H, Ph-H); 7.74 (d, 1H, H-4). $^{13}$C-NMR (CDCl$_3$, 75 MHz) δ 23.85 (CH$_2$); 45.77 (N(CH$_3$)$_2$); 50.31 (NCH$_2$); 60.55 (CH$_2$Ph); 111.40, 112.58, 113.70, 121.90, 124.74, 126.91, 127.13, 127.93, 129.03, 130.20 135.52, 137.50.

Example 5

Preparation of 2-(1-Benzyl-5-bromo-1H-indol-3-yl)-N,N-dimethyl-acetamide

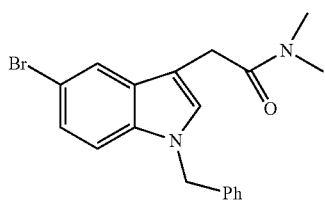 [SMILES: CN(C)C(=O)Cc1cn(Cc2ccccc2)c2ccc(Br)cc12]

In a 200 mL flask with inner thermometer and stirrer, 9.43 g (33.5 mmol) of 2-(5-bromo-1H-indol-3-yl)-N,N-dimethyl-acetamide (Example 2) in 80 mL of dry DMF is dissolved. To the solution NaH (95%, 0.885 g mg, 35 mmol) is added under an inert atmosphere. Hydrogen gas is formed, and the NaH dissolves under slight warming. A solution of benzyl chloride (4.43 g, 35 mmol) in 20 mL of DMF is added dropwise during a 10 minute period. There is again a slight exothermic reaction (45° C.), and a red-brown solution formed, which is stirred at ambient temperature for another 4 hours. The mixture is then poured into a vigorously stirred water/TBME-emulsion (4:1 v:v), and stirring is continued for an hour. This leads to the crystallization of the product, which is filtered off, washed with TBME/MeOH (9:1, v:v), subsequently triturated with methanol (50 mL), filtered off, and washed with little methanol and TBME. Colourless crystals, 8.75 g, mp=50° C. From the mother liquors, a second crop of 1.2 g, mp=149.5-150° C. is obtained. The combined yield of the title product is 80%. $^1$H-NMR (DMSO-D6, 300 MHz) δ 2.80, 3.00 (2 s, 3H each, N(CH$_3$)$_2$); 3.73 (s, 2H, CH$_2$N); 5.36 (2H, CH$_2$Ph); 7.06-7.31 (m, 7H, 5 Bn-H, H-6); 7.37 (d, 1H, J=8.8 Hz, H-7); 7.39 (s, 1H, H-2); 7.76 (d, 1H, J=1.5 Hz, H-4). $^{13}$C-NMR (DMSO-D6, 75 MHz) δ 30.90 (CH$_2$N); 35.71, 37.88 (N(CH$_3$)$_2$); 49.77 CH$_2$Ph); 108.92 (C); 112.18 (C); 112.77 (CH); 122.38 (CH); 124.38 (CH); 127.67 Bn-(CH); 128.08 (CH); 129.22 (Bn-CH); 129.66 (CH); 130.51 (C); 135.42 (C); 138.66 (C); 170.80 (CO).

Example 6

2-(3-Hydroxy-5-iodo-2-oxo-2,3-dihydro-1H-indol-3-yl)-N,N-dimethyl-acetamide

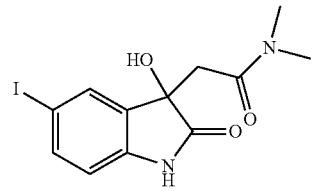 [SMILES: CN(C)C(=O)CC1(O)C(=O)Nc2ccc(I)cc21]

A 2 L flask with mechanical stirrer is charged with 5-iodo-isatin (78.1 g, 0.286 mol), malonic acid (35.7 g, 0.343 mop, and pyridine (90.4 g, 1.144 mol). The mixture is heated to 80° C. When most of the isatine has dissolved, ethyl acetate (100 mL) is added to prevent blocking of the stirrer by the precipitating pyridinium (3-hydroxy-5-iodo-2-oxo-2,3-dihydro-1H-indol-3-yl)-acetate. After 1 hour, precipitation of the latter salt starts, and when the mixture has been kept stirring for another 2 hours, a suspension of the salt in an orange solution has formed. To this is added triethyl amine (43.3 g, 0.429 mol), and the salt dissolves to give a dark solution. Then a solution of dimethyl carbamoyl chloride (40 g, 0.372 mol) in ethyl acetate (50 mL) is added dropwise during 20 minutes. A solid starts to precipitate, and the mixture is stirred for another 2 hours at 80° C. Then 4 N HCl is added (350 mL), and stirring is continued for 30 additional minutes in order to hydrolyze any excess carbamoyl chloride. The mixture is then filtered, and the filter cake is washed with 50% ethanol and the with water. After drying 72.6 g (70.5%) of a grayish powder of the title compound, mp.=246° C. $^1$H-NMR (DMSO-D6, 300 MHz) δ 2.62, 2.91 (2 s, 3 each, N(CH$_3$)$_2$); 2.91, 3.25 (AB, 2H, |$^2$J|=16.4 Hz, CH$_2$); 5.97 (br s, 1H, OH); 6.59 (d, 1H, $^3$J=7.9 Hz, H-7); 7.46 (dd, 1H, $^4$J=1.5 Hz, H-6); 7.54 (d, 1H, H-4); 10.15 (br s, 1H, NH). $^{13}$C-NMR (DMSO-D6, 75 MHz) δ 35.08, 37.48 (N(CH$_3$)$_2$); 40.86 (CH$_2$); 73.76 (C-3); 84.29 (C-5); 112.49 (C-7); 132.44 (C-4); 136.06 (C-9); 137.72 (C-6); 143.66 (C-8); 168.93 CONMe$_2$); 178.47 (C-2).

Example 7

Preparation of [2-(5-Iodo-1H-indol-3-yl)-ethyl]-dimethyl-amine

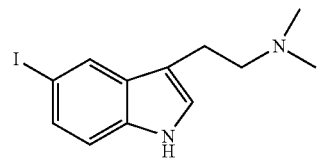

A 3 L flask is charged with 2-(5-iodo-3-hydroxy-2-oxo-2, 3-dihydro-1H-indol-3-yl)-N,N-dimethyl-acetamide (Example 6) (100 g, 0.277 mol), and 800 mL of DME. The suspension is cooled to −15° C., and sodium borohydride (31.5 g 96%, 0.832 mol) is added to this mixture, which causes a raise of the temperature by 5° C. To this, BF$_3$-etherate is added dropwise during 30 minutes (157.6 g, 1.11 mol). Initially there is a strong exothermic reaction (requires slow addition of BF3-etherate) and evolution of a gas. The temperature is maintained between −15 and −10° C. during the addition. The formed orange slurry is then allowed to warm slowly to ambient temperature (25-27° C.), and left stirring over night (17 h). To this mixture, then 4N NaOH (555 mL) is added and the mixture is heated under reflux for 50 minutes. Then DABCO (34.3 g) is added, and refluxing the mixture is continued for two additional hours. Then water (250 mL) is added, and the DME is removed on the rotavapor. The obtained orange slurry is then extracted with TBME (1000 mL, 2×600 mL), and the combined organic layers are washed with water (800 mL) and brine (700 mL), and concentrated on the rotavapor to about 600 mL. To the stirred residue, MnO$_2$ (72.4 g), is added, and the exothermic oxidation causes a temperature rise of 20° C. Stirring is continued for one hour, and then the MnO$_2$ is filtered off. Removal of the solvent from the filtrate gives a brown oil, which is dissolved in toluene. The toluene is extracted for three times with 4 N HCl (300 mL, 2×150 mL). After adjustment of the pH of the combined aqueous layers to about 10, the product is re-extracted with TBME (3×700 mL). The combined organic layers are washed with water (500 mL), and brine (500 mL), and after almost complete removal of the solvent on the rotavapor and standing over night at 4° C. some of the product crystallizes (39 g, 44.7%). Further concentration of the mother liquors and standing for two additional days gives another crop of the title product (9.5 g, 10.9%), while still about 20 g of material (about 22%) remains in the mother liquors. $^1$H-NMR (CDCl$_3$, 300 MHz): δ 2.34 (s, 6H, NMe$_2$); 2.59-2.66 (m, 2H, CH$_2$NMe$_2$); 2.85-2.92 (m, 2H, ArCH$_2$); 6.90 (d, 1H, $^3$J=2.2 Hz, H-2); 7.03 (d, 1H, $^3$J=8.4 Hz, H-7); 7.38 (dd, 1H, $^4$J=1.3 Hz, H-6); 7.91 (d, 1H, H-4); 8.56 (br s, 1H, NH). $^{13}$C-NMR (CDCl$_3$-D6, 75 MHz) δ 23.71 (ArCH$_2$); 45.65 (N(CH$_3$)$_2$); 60.32 (CH$_2$NMe$_2$); 82.77 (C-5); 113.36 (C-6); 113.86 (C-3); 122.78 (C-2); 127.87 (C-4); 130.29 (C-7); 130.33 (C-8); 135.62 (C-9).

Example 8

Preparation of [2-(1-Benzyl-5-iodo-1H-indol-3-yl)-ethyl]-dimethyl-amine

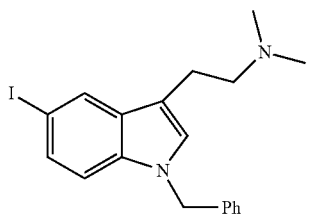 [SMILES: CN(C)CCc1cn(Cc2ccccc2)c2ccc(I)cc12]

To a solution of [2-(5-iodo-1H-indol-3-yl)-ethyl]-dimethyl-amine (Example 7) (35.0 g, 111.4 mmol) in DMF (250 mL), sodium hydride is added (2.81 g, 117 mmol) at RT in portions during 15 minutes. The mixture is then stirred for another 15 minutes, and then cooled to 4° C. A solution of benzyl chloride (14.1 g, 111.4 mmol) in DMF (50 mL) is added during 20 minutes, and the temperature is maintained during 4 to 8° C. The mixture is left stirring over night, and then most of the solvent is removed on the rotavapor. To the residue is added water (500 mL), and the product is extracted with TBME (2×250 mL). The organic layer is washed with brine (2×250 mL), and after removal of the solvent, 28.5 g of a brown oil is obtained. This is dissolved in ethyl acetate (500 mL) and the product is extracted with 4 N Hcl (550 mL). The product is liberated by adding 30% NaOH to the aqueous layer (300 mL), and re-extracted into ethyl acetate (500 mL). The organic layer is washed with brine (2×250 mL), and the solvent removed to leave 20.2 g of a brown oil which is crystallized from di-isopropyl ether and pentane to give the title product (17.3 g, 38%). Concentrating the aqueous layer of the first gives a precipitate (18.8 g) which is recrystallized from ethyl acetate (250 mL) to give 12.3 g of the N-benzyl ammonium chloride of the target.

Example 9

Preparation of 2-(5-Iodo-1H-indol-3-yl)-N,N-dimethyl-acetamide

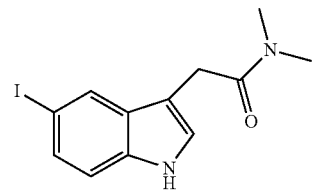 [SMILES: CN(C)C(=O)Cc1c[nH]c2ccc(I)cc12]

To a suspension of 2-(5-iodo-3-hydroxy-2-oxo-2,3-dihydro-1H-indol-3-yl)-N,N-dimethyl-acetamide (Example 6) (36.0 g, 0.1 mol) in DME (250 mL), at 20° C. boron trifluoride etherate (28.3 g, 0.2 mol) is added. Under cooling with an ice bath, borane dimethyl sulfide complex (12.0 g, 0.15 mol) is added during 10 minutes, and then the cooling bath is removed. The temperature rises slowly to 55° C., and a suspension forms at about 50° C. When the exothermic reaction has subsided, the mixture is stirred at 75° C. for another 30 minutes, and then quenched by adding 4 N NaOH (100 mL). The mixture is heated under reflux for another 30 minutes, and then filtered while still hot. Removal of the solvent on the rotavapor leads to crystallization of the product, which goes to completion on standing in the refrigerator for 12 hours. The product is filtered off, washed with cold acetone (50 mL, −20° C.) and pentane, and dried to give the title product (24.8 g, 75%) as crystals, mp.=195-200° C. $^1$H-NMR (DMSO-D6, 300 MHz) δ 2.80, 2.99 (2 s, 3H each, N(CH$_3$)$_2$); 3.69 (s, 2H, CH$_2$); 7.19 (d, 1H, $^3$J=2.4 Hz, H-2); 7.21 (d, 1H, $^3$J=8.5 Hz, H-7); 7.32 (dd, 1H, $^4$J=1.7 Hz, H-6); 7.92 (d, 1H, H-4); 11.04 (br s, 1H, NH). $^{13}$C-NMR (DMSO-D6, 75 MHz) δ 31.11 (CH$_2$); 35.70, 37.91 (N(CH$_3$)$_3$); 82.82 (C-5); 108.54 (C-3); 114.51 (C-7); 125.46 (C-2); 128.16 (C-4); 129.54 (C-6); 130.85 (C-9); 135.91 (C-8).

Example 10

Preparation of 2-(1-Benzyl-5-iodo-1H-indol-3-yl)-N,N-dimethyl-acetamide

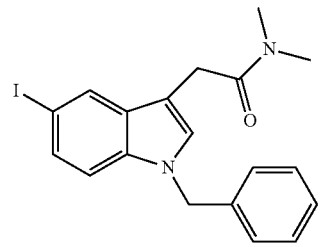 [SMILES: CN(C)C(=O)Cc1cn(Cc2ccccc2)c2ccc(I)cc12]

To a solution of 2-(5-Iodo-1H-indol-3-yl)-N,N-dimethyl-acetamide (24.7 g, 75.4 mmol) in DMF (90 mL), under an inert atmosphere sodium hydride (1.91 g 95%, 75.4 mmol) is added which leads to the formation of a pale yellow solution. When the evolution of hydrogen has ceased, benzyl chloride (9.54 g, 75.4 mmol) is added in three portions over a period of 10 minutes. The mixture warms to 60° C., and after stirring for one hour a suspension forms. On the rotavapor, a part of the DMF (about 80 mL) is removed, which leads to crystallization of the product. Water (300 mL) is added, and the crystallized product is triturated at 80° C. for one hour on the rotavapor. The product is filtered off, washed twice with water (200 mL each washing), and dried to give 26.8 g (85%) of the title compound as pale yellow crystals, mp=167-168° C. From the mother liquor, another crop (2.6 g, 8%) is obtained which is also pure. $^1$H-NMR (DMSO-D6, 300 MHz) δ 3.33, 3.72 (2 s, 3H each, N(CH$_3$)$_2$); 3.72 (s, 2H, CH$_2$CO); 5.34 (CH$_2$Ph); 7.08-7.15, 7.15-7.30 (2 m, 5H, Ph); 7.24 (d, $^3$J=8.7 Hz, H-7); 7.26 (s, 1H, H-2); 7.32 (dd, $^4$J=1.3 Hz, H-6); 7.94 (d, 1H, H-4). $^{13}$C-NMR (DMSO-D6, 75 MHz) δ 30.90 (CH$_2$CO); 35.72, 37.89 (N(CH$_3$)$_2$); 49.70 (CH$_2$Ph); 83.31 (C-5); 108.61 (C-3); 113.26 (C-2); 127.65 (2 Ph-C); 128.06 (C-6 or Ph C-4); 128.53 (C-4); 129.19 (Ph C-4 or C-6); 129.22 (2 Ph-C); 129.83 (C-7); 131.38 (Ph ipso-C); 135.79 (C-9); 138.67 (C-8); 170.82 (CONMe$_2$).

Example 11

Preparation of N,N-Dimethyl-2-(5-thiophen-2-yl-1H-indol-3-yl)-acetamide

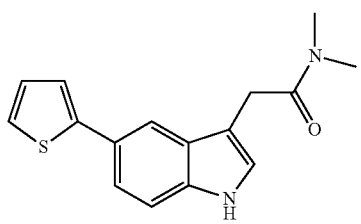 [SMILES: CN(C)C(=O)Cc1c[nH]c2ccc(-c3cccs3)cc12]

A solution of 2-(5-bromo-1H-indol-3-yl)-N,N-dimethyl-acetamide (Example 2) (227 mg, 0.81 mmol) in DME (5 mL) is degassed by sparging with argon for 10 minutes. Then thiophene-2-boronic acid (155 mg, 1.21 mmol), caesium carbonate (658 mg, 2.02 mmol), and π-allyl tri-isopropylphosphino palladium bromide (15.7 mg, 0.04 mmol) are added, and the mixture is heated under reflux. Two additional portions of caesium carbonate (103 mg, 0.81 mmol) are added after 20 hours and 24 hours to bring the reaction to completion. The black reaction mixture is poured into 2 N NaOH (10 mL), and extracted twice with ethyl acetate. After removal of the solvent, the residue is chromatographed on silica (CHCl$_3$: MeOH 29:1 v:v) to give the title product (121 mg, 54%). $^1$H-NMR (CDCl$_3$, 300 MHz) δ 2.96, 2.98 (2 s, 3H each, 2 CH$_3$); 3.77 (s, 2H, CH$_2$); 6.84 (d, $^3$J=2.2 Hz, H-2); 7.06 (dd, $^3$J=5.0 Hz, $^3$J=3.6 Hz, thiophene H-4); 7.21 (d, thiophene H-5); 7.21 (d, $^3$J=8.4 Hz, H-7); 7.25 (d, thiophene H-3); 7.40 (dd, $^4$J=1.8 Hz, H-6); 7.70 (d, H-4); 9.16 (br s, NH). $^{13}$C-NMR (CDCl$_3$, 75 MHz) δ 31.02 (CH$_2$); 36.00, 38.00 (2 CH$_3$); 109.05 (C-3); 112.17 (C-7); 116.22 (C-4); 121.08 (C-6); 122.25 (thiophene C-3); 123.70 (thiophene C-5); 124.31 (C-2); 126.29 (thiophene C-2); 127.83 (C-9); 128.15 (thiophene C-4); 136.27 (C-8); 146.56 (C-5); 172.16 (CO).

Example 12

Preparation of {2-[5-(3-Benzyloxy-prop-1-ynyl)-1H-indol-3-yl]-ethyl}-dimethyl-amine

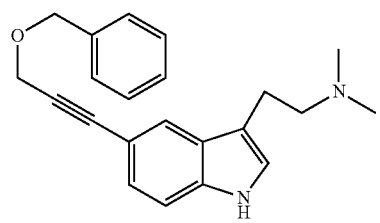 [SMILES: CN(C)CCc1c[nH]c2ccc(C#CCOCc3ccccc3)cc12]

A Schlenk flask is charged with CuI (19 mg, 0.1 mmol), Pd(PhCN)$_2$Cl$_2$ (39 mg, 0.1 mmol), piperidine (28 mL), and [2-(5-bromo-1H-indol-3-yl)-ethyl]dimethyl-amine (Example 3) (2.70 g, 10 mmol). The mixture is degassed, and then 0.4 mL of a solution of P(tBu)$_3$ in hexane (0.2 mmol) is added. The stirred yellow solution is warmed to 50° C., and a solution of benzyl propargyl ether (2.65 g, 20 mmol) in piperidine (2 mL) is added during a 5 hour period. The yellow reaction mixture is left stirring for another 15 hours when HPLC indicates complete conversion of the 5-bromotryptamine. The mixture is diluted with ethyl acetate, washed with brine (4 times 10%, 3 times saturated), and dried. After removal of the solvent, the residue is triturated with 20 mL hexane/O(i-Pr)$_2$ (1:1). The crystals which form are filtered off, washed with 4 mL of the same solvent mixture and dried in vacuo. Yield of the title compound: 2.70 g (75%), mp.=93-95° C. $^1$H-NMR (CDCl$_3$, 300 MHz) δ 2.36 (s, 6, N(CH$_3$)$_2$); 2.63-2.70 (m, 2, CH$_2$NMe$_2$); 2.90-2.97 (m, 2, Indol-CH$_2$); 4.46 (s, 2, CH$_2$-alkin); 4.72 (s, 2, CH$_2$Ph); 6.94 (d, 1, J=2.2 Hz, H-2); 7.18 (dd, 1, J=8.4 Hz, J=0.7 Hz, H-7); 7.26 (dd, 1, J=1.4 Hz, H-6); 7.32, 7.37, 7.41 (m, 5, Ph p-, m-, o-H); 7.76 (d, 1, H-4); 8.63 (br s, 1, NH). $^{13}$C-NMR (CDCl$_3$, 75 MHz) δ 23.89 (indole-CH$_2$); 45.73 (N(CH$_3$)$_2$); 58.55 (CH$_2$CC); 60.48 (CH$_2$NMe$_2$); 71.90 (CH$_2$Ph); 82.69 (CH$_2$CC); 88.57 (CH$_2$CC); 111.45 (C-7); 113.15 (C-5); 114.64 (C-3); 122.90 (C-2); 123.21 (C-4); 125.79 (C-6); 127.53 (C-9); 128.02, 128.40, 128.64 (Ph p, m, o-C); 136.34 (C-8); 137.90 (Ph ipso-C).

Example 13

Preparation of 3-(2-Dimethylamino-ethyl)-1H-indole-5-carbaldehyde

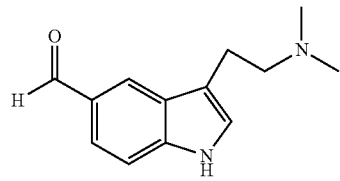 [SMILES: CN(C)CCc1c[nH]c2ccc(C=O)cc12]

To a solution of [2-(5-bromo-1H-indol-3-yl)-ethyl]-dimethyl-amine (Example 3) (15 g, 56.1 mmol) in ether (450 mL), at −75° C. a solution of tert-butyl lithium (99 ml of 1.7 N solution in hexanes, 168 mmol) is added. The mixture is stirred for 50 minutes at −75° C., and then for 30 minutes at −30° C. To the obtained beige suspension, DMF (22.5 ml) is added during 15 minutes, and then the mixture is allowed to warm to ambient temperature. The mixture is poured on water and extracted with diethyl ether (500 mL). After washing the organic layer with brine (3 times 500 mL), and drying (sodium sulfate), removal of the solvent leaves the crude aldehyde, which is recrystallized, from toluene/hexane. Yield of the title compound: 9.9 g (81.8%) yellowish plates, mp=103° C. $^1$H-NMR (CDCl$_3$, 300 MHz) δ 2.36 (s, 6H, N(CH$_3$)$_2$); 2.65-2.75 (m, 2H, CH$_2$); 2.96-3.03 (m, 2H, CH$_2$NMe$_2$); 7.08 (d, 1H, 3J=2.7 Hz, H-2); 7.33 (d, 1H, $^3$J=8.4 Hz, H-7); 7.70 (dd, 1H, $^4$J=1.7 Hz, H-6); 8.13 (d, 1H, H-4); 8.74 (br s, 1H, NH); 10.02 (s, 1H, CHO). $^{13}$C-NMR (CDCl$_3$, 75 MHz) δ 23.91 (CH$_2$); 45.76 (CH$_3$); 60.40 (CH$_2$N); 111.85 (C-7); 116.68 (C-3); 122.87 (C-6); 123.61 (C-2); 124.04 (C-4); 127.68 (C-9); 129.35 (C-5); 140.06 (C-8); 192.56 (CHO).

Example 14

Preparation of Dimethyl-[2-(5-vinyl-1H-indol-3-yl)-ethyl]-amine

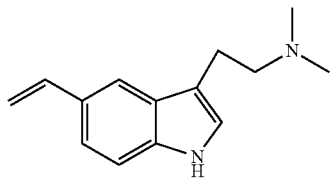 [SMILES: C=Cc1ccc2[nH]cc(CCN(C)C)c2c1]

To a solution of 3-(2-dimethylamino-ethyl)-1H-Indole-5-carbaldehyde (Example 13) (0.216 g, 1 mmol) in THF (5 mL), methyl triphenyl phosphonium bromide (0.393 g, 1.1 mmol) is added. To the obtained slurry, under an argon atmosphere potassium tert-butoxide (0.118 g, 1.05 mmol) is added in three portions at ambient temperature. When thin layer chromatography (TLC) indicates complete conversion of the aldehyde, the mixture is poured on ice and extracted with ethyl acetate. Removal of the solvent gives a residue which is chromatographed on silica (25 g, CHCl$_3$, MeOH, NEt$_3$ 19:1:0.5 v:v:v) to give the title product as pale yellow oil (0.190 g, 88%). $^1$H-NMR (CDCl$_3$, 300 MHz) δ 2.37 (s, 6H, N(CH$_3$)$_2$); 2.64-2.70 (m, 2H, CH$_2$NMe$_2$); 2.92-2.99 (m, 2H, CH$_2$); 5.13 (d, 1H, J=10.9 Hz, cis H$_2$C=CH); 5.69 (d, 1H, J=17.6 Hz, trans H$_2$C=CH); 6.84 (dd, 1H, H$_2$C=CH); 6.94 (br s, 1H, H-2); 7.24 (d, 1H, J=8.2 Hz, H-7); 7.31 (dd, J=1.8 Hz, H-6); 7.58 (d, 1H, H-4); 8.66 (br 5, 1H, NH). $^{13}$C-NMR (CDCl$_3$, 75 MHz) δ 24.00 (CH$_2$); 45.73 (N(CH$_3$)$_2$); 60.62 (CH$_2$NMe$_2$); 110.93 (H$_2$C=CH); 111.50 (C-7); 114.66 (C-3); 117.41 (C-4); 120.20 (C-6); 122.42 (C-2); 127.83 (C-5); 129.34 (C-9); 136.45 (C-8); 138.22 (H$_2$C=CH).

Example 15

Preparation of [3-(2-Dimethylamino-ethyl)-1H-indol-5-yl]-methanol

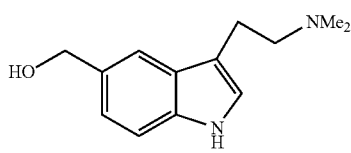 [SMILES: CN(C)CCc1c[nH]c2ccc(CO)cc12]

A 50 ml hydrogenation bomb is charged with 3-(2-dimethylamino-ethyl)-1H-indole-5-carbaldehyde (Example 13) (1.0 g, 4.62 mmol) and methanol (10 mL). The bomb is purged with hydrogen (three times to 200 psi and release to atmospheric pressure), and then pressurised to 200 psi. After stirring for one hour, the pressure is released, and a solution of [Rh DiPFc (COD)]BF$_4$ (6.6 mg, S/C=500) in methanol (1 ml) is added through a septum port. The bomb is pressurized with hydrogen to 200 psi, and left stirring at ambient temperature for 18 hours. Removal of the solvent from the hydrogenation mixture gives the title product (1.05 g, quant.) as an oil.

$^1$H-NMR (CDCl$_3$, 300 MHz) δ 2.21 (s, 6H, N(CH$_3$)$_2$); 2.49-2.60 (m, 2H, CH$_2$NMe$_2$); 2.73-2.83 (m, 2H, CH$_2$CH$_2$NMe$_2$); 4.63 (s, 2H, CH$_2$OH); 4.85 (br s, 1H, OH); 6.76 (s, 1H, H-2); 7.03 (dd, 1H, $^3$J=8.2 Hz, $^4$J=1.5 Hz, H-6); 7.14 (d, 1H, H-7); 7.41 (d, 1H, H-4); 8.96 (br s, 1H, NH). $^{13}$C-NMR (CDCl$_3$, 75 MHz) δ 22.99 (CH$_2$); 44.73 (CH$_3$); 59.71 (CH$_2$N); 66.11 (CH$_2$OH); 111.62 (C-7); 113.07 (C-3); 117.62 (C-4); 122.01 (C-6); 122.67 (C-2); 127.48 (C-9); 132.38 (C-5); 136.15 (C-8)

Example 16

Preparation of 3-Dimethyl-carbamoylmethyl-3-hydroxy-2-oxo-2,3-dihydro-1H-indole-5-carboxylic acid ethyl ester

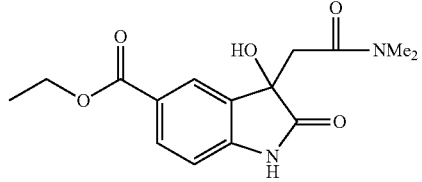 [SMILES: CCOC(=O)c1ccc2c(c1)C(O)(CC(=O)N(C)C)C(=O)N2]

A pressure vessel is charged with 2-(5-Bromo-3-hydroxy-2-oxo-2,3-dihydro-1H-indol-3-yl)-N,N-dimethyl-acetamide (21.92 g, 70 mmol), Pd(dppp)Cl2 (4.13 g, 7 mmol), triethyl amine (28.4 g, 0.28 mol) and ethanol (405 ml, solvent). After assembling and purging with nitrogen, the vessel is charged with carbon monoxide to a pressure of 20 bar, and the carbonylation is performed at 120° C. over night. The reaction mixture is filtered through a celite pad, and the solvent is removed on the rotavapor. The residue is kept under reflux with ethyl acetate (750 mL), and filtered. After washing the filter cake for three times with ethyl acetate (3*100 mL), the filtrate is concentrated (to ca. 300 mL), and the obtained suspension is left at 0° C. over night. The product is filtered off and dried to give 19.0 g (87%) of the title compound in the form of beige crystals. $^1$H-NMR (CDCl$_3$, 300 MHz) δ 1.29 (tr. 3H, J=7.0 Hz); 2.62, 2.94 (2 s, 3 each, N(CH$_3$)$_2$); 2.98, 3.32 (AB, 2J=18.2 Hz, CH$_2$NMe$_2$); 417-4.34 (m, 2H, CH$_2$Me); 6.02 (s, 1H, OH); 6.82 (d, 1H, J=7.6 Hz, H-7); 7.79 (br s, 1H, H-4); 7.81 (dd, 1H, J=7.6 Hz, J=1.8 Hz, H-6). $^{13}$C-NMR (CDCl$_3$, 75 MHz) □ 15.16 (CH$_3$); 35.13, 37.56 (N(CH$_3$)$_2$); 46.49 (CH$_2$NMe$_2$); 61.02 (CH$_2$Me); 73.56 (C-3); 109.75 (C-7); 123.16, 124.73 (C-6); 131.72 (C-4); 133.49, 148.53 (C-8); 166.34, 168.78, 179.23 (3 C=O).

Example 17

Preparation of 3-(2-dimethylamino-ethyl)-1H-indole-5-carbonitrile

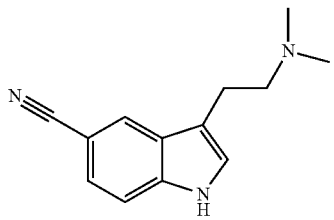 [SMILES: CN(C)CCc1c[nH]c2ccc(C#N)cc12]

Under an inert atmosphere a flask is charged with [2-(5-bromo-1H-indol-3-yl)-ethyl]-dimethyl-amine (Example 3) (1.0 g, 3.74 mmol), zinc cyanide (0.235 g, 2 mmol), $Pd_2(dba)_3 \cdot xCHCl_3$ (0.194 mg, 5 mol %), dppf (bis-diphenylphosphino ferrocene) (0.207 g, 0.374 mmol, 10 mol %), and DMF (12 mL). The orange slurry is heated to 110° C. and stirred for 21 hours. To the black suspension which has formed, THF (100 mL) is added, and this is extracted with 1 N NaOH (100 mL). The organic layer is washed with water twice (50 mL each), dried and removal of the solvent gives the title product (0.67 g, 84%) as brown solid.

$^1$H-NMR (CDCl$_3$, 300 MHz) δ 2.35 (s, 6H, 2 CH$_3$); 2.67 (m, 2H, CH$_2$NMe$_2$); 2.91 (m, 2H, CH$_2$); 7.01 (s, 1H, H-2); 7.13 (d, 1H, $^3$J=8.3 Hz, H-7); 7.26 (dd, 1H, $^4$J=1.6 Hz, H-6); 7.87 (d, 1H, H-4); 9.80 (br s, 1H, NH). $^{13}$C-NMR (CDCl$_3$, 75 MHz) δ 23.48 (CH$_2$); 45.42 (CH$_3$); 60.06 (CH$_2$N); 101.75 (C-5); 112.24 (C-7); 114.74 (C-3); 121.41 (CN); 124.49 (C-4); 124.62 (C-6); 124.75 (C-2); 127.31 (C-9); 138.47 (C-8).

Example 18

Preparation of 2-(1-Benzyl-3-hydroxy-2-oxo-2,3-dihydro-1H-indol-3-yl)-N,N-dimethyl-acetamide

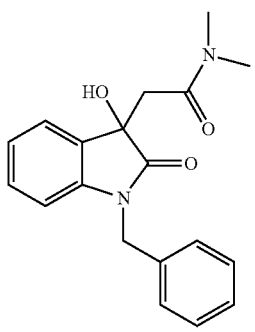 [SMILES: CN(C)C(=O)CC1(O)C(=O)N(Cc2ccccc2)c2ccccc21]

A 500 mL flask is charged with N-benzyl isatin (55 g, 0.231 mol), malonic acid (28.95 g, 0.278 mol), and pyridine (73.4 g, 0.927 mol). To the formed red suspension, ethyl acetate (50 mL) is added, and the stirred mixture is heated to 80° C. After about 30 minutes a solution has formed which is kept stirring at 80° C. until no further formation of carbon dioxide is observed (about 2.5 h). Then triethyl amine (35.2 g, 0.347 mol) is added, and the mixture is stirred for another 10 minutes at 80° C. To the dark red solution, then dropwise (exothermicl) dimethyl carbamoyl chloride (32.4 g, 0.301 mol) is added during 10 minutes. When the evolution of carbon dioxide ceases, the mixture is kept stirring at 80° C. for another two hours, and then the solvent is removed from the brown suspension on the rotavapor. To the residue, HCl (4N, 0.2 L) is added, and the formed suspension is stirred for one hour at 80° C. After cooling and standing in the refrigerator over night, the crystals are filtered off, washed twice with water (about 150 mL each wash) and dried in vacuo to give light brown crystals. Yield of the title compound: 66.7 g (88.7% based on N-benzyl isatin). $^1$H-NMR (CDCl$_3$, 300 MHz) δ 2.69, 3.03 (AB, 2H, $^2$J=16.1 Hz, CH$_2$CONMe$_2$); 2.91, 2.99 (2 s, 3 each, N(CH$_3$)$_2$); 4.87, 4.89 (AB, 2H, $^2$J=15.8 Hz, CH$_2$Ph); 6.70 (d, 1H, J=7.7 Hz, H-7); 7.01 (dtr, J=7.7 Hz, J=1.1 Hz, H-5); 7.17 (dtr, 1H, J=7.7 Hz, J=11 Hz, H-6); 7.21-7.34 (m, 5H, Ph); 7.49 (dd, J=7.3 Hz, J=1.8 Hz, H-4). $^{13}$C-NMR (CDCl$_3$, 75 MHz) δ 35.64, 37.66 N(CH$_3$)$_2$; 38.21 (CH$_2$CONMe$_2$); 44.02 (CH$_2$Ph); 74.61 (C-3); 109.70 (C-7); 123.38 (C-5); 124.63 (C-4); 127.51, 127.90, 129.03 (Ph ortho-C, para-C, meta-C); 129.82 (C-6); 131.15 (C-9); 135.77 (Ph ipso-C); 142.47 (C-8); 171.18 (CONMe$_2$); 176.51 (C-2).

Example 19

Preparation of 2-(1-Benzyl-2-oxo-1,2-dihydro-indol-3-ylidene)-N,N-dimethyl-acetamide

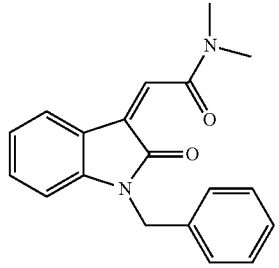 [SMILES: CN(C)C(=O)/C=C1\C(=O)N(Cc2ccccc2)c2ccccc21]

A mixture of 2-(1-benzyl-3-hydroxy-2-oxo-2,3-dihydro-1H-indol-3-yl)-N,N-dimethyl-acetamide (Example 21) (1.0 g, 3.08 mmol), acetic acid (8 mL) and acetic anhydride (2 mL) is heated under reflux for two hours, and then poured in water (100 ml). Extraction with CHCl$_3$ gives 1.2 g of a yellow oil which is chromatographed on silica gel (ethyl acetate:hexanes 1:1 v:v) to give the E-stereoisomer (333 mg, less polar) of the title compound and its Z-stereoisomer (110 mg).

(E)-stereoisomer (kinetic product, major): $^1$H-NMR (CDCl$_3$, 300 MHz) δ 3.11, 3.13 (2 s, 3 each, N(CH$_3$)$_2$); 4.94 (s, 2, CH$_2$Ph); 6.67 (d, 1, J=7.9 Hz, H-7); 6.96 ("dtr", 1, J=7.6 Hz, J=0.9 Hz, H-5); 7.18 ("dtr", 1, J=7.8 Hz, J=1.2 Hz, H-6); 7.23, 7.29 (m, 5, Ph-H); 7.27 (s, 1, CHC(O)NMe$_2$); 7.81 ("dd", 1, J=7.8 Hz, J=0.9 Hz, H-4). $^{13}$C-NMR (CDCl$_3$, 75 MHz) δ 35.27, 37.97 (N(CH$_3$)$_2$); 44.16 (CH$_2$Ph); 109.40 (C-7); 120.28 (C-9); 122.92 (C-5); 125.98 (C-4); 126.02 (CHCONMe$_2$); 127.47 (Ph-ortho C); 127.87 (Ph para-C); 128.98 (Ph meta-C); 131.31 (C-6); 132.72 (C-3); 135.79 (C-15); 144.15 (C-8); 166.08 (C-2); 167.79 (CONMe$_2$). (Z)-stereoisomer (thermodynamic product): $^1$H-NMR (CDCl$_3$, 300 MHz) δ 3.07, 3.14 (2 s, 3 each, N(CH$_3$)$_2$); 4.90 (s, 2, CH$_2$Ph); 6.68 (d, 1, J=7.9 Hz, H-7); 6.91 (s, 1, CHC(O)NMe$_2$); 7.00 ("dtr", 1, J=7.5 Hz, J=0.9 Hz, H-5); 7.19 ("dtr", J=7.8 Hz, J=0.9 Hz, H-6); 7.25-7.35 (m, 5 Ph-H); 7.43 ("dd", J=7.4 Hz, J=0.6 Hz, H-4). $^{13}$C-NMR (CDCl$_3$, 75 MHz) δ 34.78, 37.66 (N(CH$_3$)$_2$); 43.94 (CH$_2$Ph); 109.59 (C-7);

120.96 (C-4); 121.63 (C-9); 122.52 (C-5); 126.73 (CHCONMe$_2$); 127.56 (Ph-ortho C); 127.85 (Ph para-C); 128.96 (Ph meta-C); 130.70 (C-6); 129.67 (C-3); 135.84 (C-15); 143.22 (C-8); 165.56 (C-2); 166.51 (CONMe$_2$).

Example 20

Preparation of 2-(1-Benzyl-2-oxo-2,3-dihydro-1H-indol-3-yl)-N,N-dimethyl-acetamide

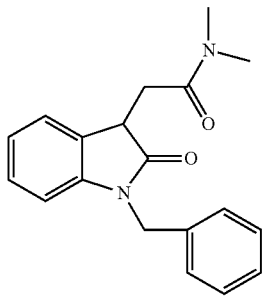 [SMILES: CN(C)C(=O)CC1C(=O)N(Cc2ccccc2)c2ccccc21]

A flask is charged with 2-(1-benzyl-3-hydroxy-2-oxo-2,3-dihydro-1H-indol-3-yl)-N,N-dimethyl-acetamide (Example 19) (10.0 g, 30.8 mmol), acetic acid (250 mL), acetic anhydride (100 g), and Zn-dust (20 g). The mixture is kept under reflux, until all of the starting material is consumed (3 h). The solids are then filtered off, and from the filtrate the solvent is removed to leave an oil which crystallizes to a pale brown solid on treatment with di-iso-propyl ether. Yield of the title compound: 9.2 g (96.8%). $^1$H-NMR (CDCl$_3$, 300 MHz) δ 2.73 (dd, 1, $^2$J=16.5 Hz, J=9.4 Hz, CH$_2$NMe$_2$); 3.00, 3.01 (2 s, 6, N(CH$_3$)$_2$); 3.20 (dd, 1, J=3.2 Hz, CH$_2$NMe$_2$); 4.06 (dd, 1, H-3); 4.90, 4.97 (AB, 2, $_2$J=15.6 Hz, CH$_2$N); 6.70 (d, 1, J=7.9 Hz, H-7); 6.97 ("dtr", J=7.5 Hz, J=1.2 Hz, H-5); 7.13 ("dtr", J=7.8 Hz, J=1.2 Hz, H-6); 7.22-7.29, 7.29-7.33 (m, 5, 5 Ph-H); 7.38 (br d, 1, J=7.5 Hz, H-4). $^{13}$C-NMR (CDCl$_3$, 75 MHz) δ 35.25 (CH$_2$NMe$_2$); 36.07, 37.51 (N(CH$_3$)$_2$); 42.59 (C-3); 44.28 (NCH$_2$Ph); 109.12 (C-7); 122.66 (C-5); 124.85 (C-4); 127.49 (Ph meta-C); 127.71 (Ph para-C); 128.04 (C-6); 128.92 (Ph ortho-C); 129.63 (C-9); 136.19 (Ph ipso-C); 143.52 (C-8); 170.00 (CONMe$_2$); 178.02 (C-2),

Example 21

Preparation of 2-(1-Benzyl-5-chloro-3-hydroxy-2-oxo-2,3-dihydro-1H-indol-3-yl)-N,N-dimethyl-acetamide

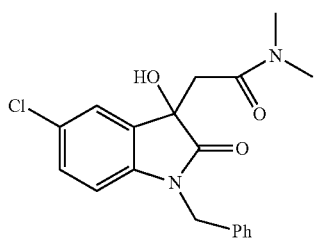 [SMILES: CN(C)C(=O)CC1(O)C(=O)N(Cc2ccccc2)c2ccc(Cl)cc21]

A flask is charged with 2-(1-benzyl-3-hydroxy-2-oxo-2,3-dihydro-1H-indol-3-yl)-N,N-dimethyl-acetamide (Example 18) (10 g, 30.83 mmol), N-chloro succinimide (NCS) (4.12 g, 30.83 mmol), acetic acid (40 mL), and toluene (20 mL). The orange suspension is then stirred over night and becomes a homogeneous solution. After the addition of about 5 mL of water, the solvent is removed on the rotavapor. To the residue, water is added, and the product is extracted with chloroform. After drying and removal of solvent 11 g of crude product is obtained which after chromatography on silica (toluene:ethyl acetate 1:1) gives the title product (9.76 g, 88%) as yellow foam. $^1$H-NMR (CDCl$_3$, 300 MHz) δ 2.74, 3.08 (AB, 2H, $^2$J=16.3 Hz, CH$_2$CONMe$_2$); 4.85 (s, 2H, NCH2Ph); 6.32 (br s, 1H, OH); 6.58 (d, 1H, $^3$J=8.2 Hz, H-7); 7.10 (dd, 1H, 4J=2.0 Hz, H-6); 7.13-7.32 (m, 5H, Ph); 7.46 (d, 1H, H-4). $^{13}$C-NMR (CDCl$_3$, 75 MHz) δ 35.77, 37.77 (N(CH$_3$)$_2$); 38.80 (CH$_2$CONMe$_2$); 44.27 (CH$_2$Ph); 74.65 (C-3); 110.72 (C-7); 125.10 (C-4); 127.33 (Ph ortho-C); 127.90 (Ph para-C); 128.54 (C-5); 129.00 (Ph meta-C); 129.49 (C-6); 132.80 (C-9); 135.26 (C-15); 141.08 (C-8); 170.31 (C-11); 175.96 (C-2).

Example 22

Preparation of Acetic acid 1-benzyl-3-dimethyl-carbamoylmethyl-3-hydroxy-2-oxo-2,3-dihydro-1H-indol-5-ylmethyl ester

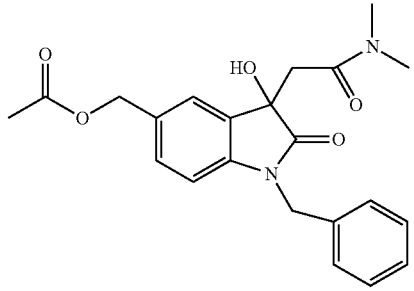 [SMILES: CC(=O)OCc1ccc2c(c1)C(O)(CC(=O)N(C)C)C(=O)N2Cc1ccccc1]

A 4 L flask is charged with para-formaldehyde (92.6 g, 3.082 mol), glacial acetic acid (400 mL), and sulfuric acid (60.5 g, 0.617 mol). The mixture is heated at 90° C. until a homogeneous solution forms. To this, during 90 minutes a solution of 2-(1-benzyl-3-hydroxy-2-oxo-2,3-dihydro-1H-indol-3-yl)-N,N-dimethyl-acetamide (Example 18) (200 g, 0.617 mol) in acetic acid (1000 mL) and water (22.2 mL) is added. The mixture is kept at 90° C. for another 30 minutes, until all of the starting material is consumed (HPLC). The reaction is then quenched by the addition of sodium acetate (50.5 g), and the solvent is removed on the rotavapor. The remaining red oil is stirred with water (1000 mL), and this mixture is extracted with chloroform (2×500 mL). After drying the combined organic layers and removal of the solvent, the title product is obtained as a red foam (220 g, 90%). This material contains about 35% of by-products, the main one (about 30%) being the diaryl methane, and products formed by elimination of the 3-OH group. HPLC-conditions: column 12.5 m C18 modified, flow: 1 mL/min, gradient 25% acetonitrile/75% water to 100% acetonitrile in 10 minutes, then another 3 minutes acetonitrile. Detection at 254/210 nm. Retention times: 5-hydroxymethylated product: 3.91 min; starting material 5.40 min; 5-acetoxymethyl title product: 5.65 min; 6.4-7.3 min: diphenylmethane derivatives and isatylidenes. $^1$H-NMR (CDCl$_3$, 300 MHz) δ 2.06 (s, 3, CH$_3$CO); 2.71, 3.05 (AB, 2, J=16.1 Hz, CH$_2$CO); 2.93, 3.02 (2 s, 3 each, N(CH$_3$)$_2$); 4.87, 4.90 (AB, 2, J=15.6 Hz, CH$_2$N); 5.00 (s, 2, CH$_2$OAc); 6.43 (s, 1, OH); 6.68 (d, 1, J=7.9 Hz, H-7); 7.18 (dd, 1, J=8.2 Hz, J=1.8 Hz, H-6); 7.23-7.33 (m, 5H, 5 Ph-H); 7.50 (d, J=1.8 Hz, 1, H-4). $^{13}$C-NMR (CDCl$_3$, 75 MHz) δ 21.38 (CH$_3$COO); 35.78, 37.78 (N(CH$_3$)$_2$); 38.31 (CH$_2$CO); 44.22 (NCH$_2$); 66.46 (CH$_2$OAc); 74.60 (C-3); 109.62 (C-7); 125.15 (C-4); 127.47 (Bn meta C); 127.62 (Bn para-C); 129.01 (Bn ortho-C); 130.31 (C-6); 131.05 (C-5); 131.47

(C-9); 135.56 (Bn ipso-C); 142.56 (C-8); 170.89, 170.90 (CH₃COO, CONMe₂); 176.33 (C-2).

Example 23

Preparation of 2-(1-Benzyl-3-hydroxy-5-hydroxy-methyl-2-oxo-2,3-dihydro-1H-indol-3-yl)-N,N-dimethyl-acetamide

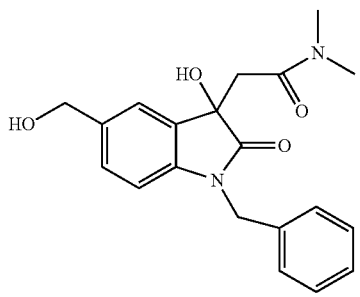 [SMILES: CN(C)C(=O)CC1(O)C(=O)N(Cc2ccccc2)c2ccc(CO)cc21]

To a solution of acetic acid with 1-benzyl-3-dimethyl-carbamoylmethyl-3-hydroxy-2-oxo-2,3-dihydro-1H-indol-5-ylmethyl ester (Example 22) (18.3 g, 46.2 mmol) in methanol (400 mL), potassium carbonate (20 g) is added, and the mixture is kept under reflux for 16 hours (no starting material by HPLC). The mixture is then neutralized with 2 N sulfuric acid, and the methanol is removed on the rotavapor. The remaining aqueous phase is extracted with chloroform (2×200 mL), the combined extracts are washed with water (2×200 mL), dried and after removal of the solvent the title product is obtained as light brown foam (16.8 g, quantitative). $^1$H-NMR (CDCl₃, 300 MHz) δ 2.74, 3.03 (AB, 2, $^2$J=15.8 Hz, CH₂CONMe₂); 2.86, 2.91 (2 s, 3 each, N(CH₃)₂); 4.52 (s, 2, CH₂OH); 4.84, 4.86 (AB, 2, $^2$J=15.8 Hz, NCH₂); 6.62 (d, 1, $^3$J=7.9 Hz, H-7); 7.11 (dd, 1, $^4$J=1.5 Hz, H-6); 7.21-7.26 (m, 5, Ph); 7.47 (d, 1, H-4). $^{13}$C-NMR (CDCl₃, 75 MHz) δ 35.74, 37.78 (N(CH₃)₂); 38.74 (CH₂CONMe₂); 44.16 (NCH₂); 65.08 (CH₂OH); 74.61 (C-3); 109.56 (C-7); 123.71 (C-4); 127.43 (Bn ortho-C); 127.81 (Bn para-C); 128.70 (C-6); 128.96 (Bn meta-C); 131.27 (C-9); 135.73 (Bn ipso-C); 136.37 (C-5); 141.91 (C-8); 170.66 (C-11); 176.69 (C-2).

Example 24

Preparation of 2-(1-Benzyl-5-formyl-3-hydroxy-2-oxo-2,3-dihydro-1H-indol-3-yl)-N,N-dimethyl-acetamide

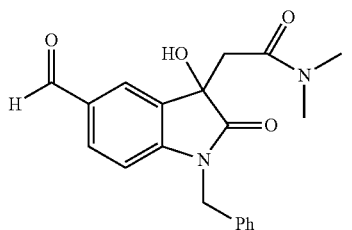 [SMILES: CN(C)C(=O)CC1(O)C(=O)N(Cc2ccccc2)c2ccc(C=O)cc21]

Under inert atmosphere, a flask is charged with manganese dioxide (8.7 g, 0.1 mol) and 2-(1-benzyl-3-hydroxy-5-hydroxy-methyl-2-oxo-2,3-dihydro-1H-indol-3-yl)-N,N-dimethyl-acetamide (Example 23) (3.54 g, 0.01 mol). To this, mol sieve (4 A, 2 g) and dichloromethane (100 mL) are added, and the mixture is heated under reflux for six hours. The mixture is then filtered, and evaporation of the solvent leaves 3.5 g of a dark brown foam. This is chromatographed on silica (ethyl acetate) to give 1.8 g (50%) of the title product as pale yellow foam. $^1$H-NMR (CDCl₃, 300 MHz) δ 2.82, 3.13 (AB, 2H, $^2$J=16.1 Hz, CH₂NMe₂); 2.95, 2.98 (2 s, 3H each, N(CH₃)₂); 4.93, 4.94 (AB, 2H, $^2$J=16 Hz, NCH₂Ph); 6.11 (s, 1H, OH); 6.82 (d, 1H, $^3$J=7.9 Hz, H-7); 7.23-7.38 (m, 5H, Ph); 7.72 (dd, 1H, $^4$J=1.5 Hz, H-6); 8.00 (d, 1H, H-4); 9.83 (s, 1H, CHO). $^{13}$C-NMR (CDCl₃, 75 MHz) δ 35.76, 37.70 (N(CH₃)₂); 38.72 (CH₂CONMe₂); 44.42 (NCH₂Ph); 74.06 (C-3); 109.80 (C-7); 125.38 (C-4); 127.42 (Bn ortho-C); 128.14 (Bn para-C); 129.16 (Bn meta-C); 132.00, 132.31 (C-5, C-9); 133.49 (C-6); 135.04 (Ph ipso-C); 148.24 (C-8); 170.22 (CONMe₂); 176.69 (C-2); 190.80 (CHO).

Example 25

Preparation of 1-Allyl-1H-indole-2,3-dione

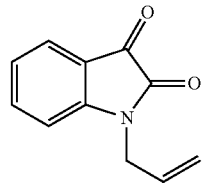

A 500 mL flask is charged with isatin (50 g, 339 mmol), allyl chloride (33.8 g, 441 mmol), potassium carbonate (93.9 g, 679 mmol), and DMF (100 mL). The mixture is stirred at 70° C. for 14 hours (complete conversion by TLC), and then diluted with DMF. After filtration over a pad of cellite and removal of the solvent, the product remained as red crystals (68 g) which are used directly in the next step. $^1$HNMR (CDCl₃, 300 MHz) δ 4.34 (dtr, 1H, 3 J=5.3 Hz, $^4$J=1.8 Hz, NCH₂CHC=CH₂); 5.27 (dm, 1H, $^3$J=10.3 Hz, NCH₂CHC=CH$_{cis}$); 5.30 (dm, 1H, $^3$J=17.0 Hz, NCH₂CHC=CH$_{trans}$); 5.82 (ddtr, NCH₂CHC=CH₂); 6.87 (d, 1H, 3J=7.9 Hz, H-7); 7.09 (br tr, 1H, $^3$J=7.3 Hz, H-5); 7.55 (dtr, 1H, 3 J=8 Hz, H-6); 7.57 (d m, 1H, $^3$J=7.3 Hz, H-4). $^{13}$C-NMR (CDCl₃, 75 MHz) δ 42.82 (NCH2); 111.11 (C-7); 117.77 (C-9); 118.80 (CH=CH₂); 123.96 (C-5); 125.50 (C-4); 130.51 (CH=CH₂); 138.48 (C-6); 150.96 (C-8); 158.02 (C-2); 183.29 (C-3).

Example 26

Preparation of 2-(1-Allyl-3-hydroxy-2-oxo-2,3-dihydro-1H-indol-3-yl)-N,N-dimethyl-acetamide

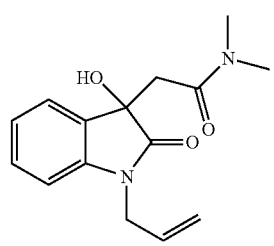 [SMILES: C=CCN1C(=O)C(O)(CC(=O)N(C)C)c2ccccc21]

A 1 L flask is charged with 1-allyl-1H-indole-2,3-dione (Example 25) (63.6 g, 339 mmol), and pyridine (107.5 g, 1.36 mol). To this, malonic acid (42.4 g, 407 mmol) is added, which leads to a slight exothermic reaction. The obtained slurry is heated at 80° C. until the formation of carbon dioxide ceases and TLC indicates no starting material to be present. To the reddish solution, triethyl amine (51.6 g, 441 mmol) is added, and the mixture is stirred for another 10 minutes when a dark red solution forms. To this solution, dimethyl carbamoyl chloride (47.5 g, 441 mmol) is added during 15 minutes which gives an exothermic reaction with vigorous formation of carbon dioxide. The mixture is stirred for another 15 minutes, and then the solvent is removed on the rotavapor. To the residue, water (about 300 mL) and chloroform (about 300 mL) are added. The pH is adjusted to slightly acidic (6.0) by adding 2 N HCl. The organic layer is separated off, and the aqueous layer extracted once more with chloroform (100 mL). The combined organic layers are dried (sodium sulfate), filtered and, after removal of the solvent, a light brown solid is obtained (107 g). This is triturated with cold water (500 mL, 4° C.), and filtered. After washing and drying the title product is obtained as beige crystals (76.6 g, 82%). $^1$HNMR (DMSO, 300 MHz) δ 2.63, 2.94 (2 s, 3H each, N(CH$_3$)$_2$); 3.04, 3.30 (Aft 2H, $^2$J=16.4 Hz, CH$_2$CONMe$_2$); 4.28, 4.35 (ABdtr, 2H, $^2$J=16.3 Hz, NCH$_2$CH═CH$_2$); 5.15 (ddtr, 1H, $^2$J=1.5 Hz, $^3$J=10.3 Hz, $^4$J=1.5 Hz, CH$_2$CH═CH$_{cis}$); 5.38 (ddtr, 1H, $^3$J=17.3 Hz, $^4$J=1.8 Hz, CH$_2$CH═CH$_{trans}$); 5.84 (ddtr, 1H, 3J=4.7 Hz, CH$_2$CH═CH$_2$); 6.82 (d, 1H, J=7.6 Hz, H-7); 6.95 (dtr, 1H, $^3$J=7.6 Hz, $^4$J=1.2 Hz, H-5); 7.21 (dtr, 1H, $^3$J=7.6 Hz, $^4$J=1.5 Hz, H-6); 7.32 (dd, 1H, $^3$J=7.3 Hz, $^4$J=1.2 Hz, H-4). $^{13}$C-NMR (DMSO, 75 MHz) δ 35.22, 37.67 (N(CH$_3$)$_2$); 41.23 (CH$_2$CONMe$_2$); 42.27 (NCH$_2$CH═CH$_2$); 73.69 (C-3); 109.36 (C-7); 117.34 (NCH$_2$CH═CH$_2$); 122.22 (C-5); 123.66 (C-4); 129.29 (C-6); 132.39 (C-9); 132.75 (NCH$_2$CH═CH$_2$); 144.30 (C-8); 168.79 (CONMe$_2$); 177.13 (C-2).

Example 27

Preparation of 2-(1-Allyl-3-hydroxy-5-hydroxy-methyl-2-oxo-2,3-dihydro-1H-indol-3-yl)-N,N-dimethyl-acetamide

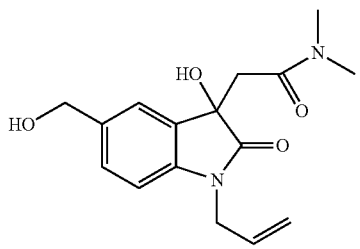 [SMILES: C=CCN1C(=O)C(O)(CC(=O)N(C)C)c2cc(CO)ccc21]

To a suspension of para-formaldehyde (36.2 g, 1.13 mol) in 150 ml of glacial acetic acid, sulfuric acid (22.2 g, 0.226 mol) is added and the mixture heated at 80° C., until a clear solution has been formed. To this, during 45 minutes a solution of 2-(1-allyl-3-hydroxy-2-oxo-2,3-dihydro-1H-indol-3-yl)-N,N-dimethyl-acetamide (example 26) (62 g, 226 mmol) in a mixture of glacial acetic acid (350 mL) and water (10 mL) is added.

The red reaction mixture is stirred for another hour at 80° C., and by then all of the starting material is consumed (HPLC). Sodium acetate (46.3 g, 564 mmol) is added, and after stirring for 5 minutes an orange suspension forms. The solvent is removed on the rotavapor, and to the residue water (about 250 mL) is added. Extraction with chloroform (2×200 mL), drying the organic layer and removal of the solvent leaves the crude title product (77.7 g, quant.) as a red oil. After chromatographic purification white crystals, mp=125° C. $^1$H-NMR (CDCl$_3$, 300 MHz) δ 2.71, 2.94 (AB, 2H, $^2$J=16.1 Hz, CH$_2$CONMe$_2$); 2.83, 2.84 (2 s, 3H each, N(CH$_3$)$_2$); 4.19, 4.25 (AB$_{Allyl}$, 2 H, $^2$J=16.4 Hz, $^3$J=5.3 Hz, NCH$_2$); 4.47 (s, 2H, CH$_2$OH); 5.12 (dd, 1H, $^2$J=1.2 Hz, $^3$J=10.3 Hz, cis CH═CH$_2$), 5.51 (dd, 1H, $^3$J=17.3 Hz, trans CH═CH$_2$); 5.75 (ddtr, 1H, CH═CH$_2$); 6.21 (br s, 1H, OH); 6.70 (d, 1H, $^3$J=7.9 Hz, H-7); 7.15 (dd, 1H, $^4$J=1.5 Hz, H-6); 7.37 (d, 1H, H-4), $^{13}$C-NMR (CDCl$_3$, 75 MHz) δ 35.71, 37.84 (N(CH$_3$)$_2$); 38.87 (CH$_2$CONMe$_2$); 42.67 (NCH$_2$); 64.80 (CH$_2$OH); 74.46 (C-3); 109.36 (C-7); 117.73 (CH═CH$_2$); 123.43 (C-4); 128.63 (C-6); 131.00 (C-9); 131.33 (CH═CH$_2$); 136.35 (C-5); 141.89 (C-8); 170.53 (C-11); 176.36 (C-2).

Example 28

Preparation of 1-benzyl-1H-spiro[indole-3,3'-oxolano]-2,5'-dione

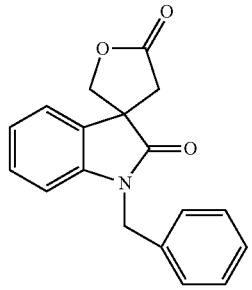 [SMILES: O=C1CC2(CO1)C(=O)N(Cc1ccccc1)c1ccccc12]

A solution of 2-(1-Benzyl-2-oxo-2,3-dihydro-1H-indol-3-yl)-N,N-dimethyl-acetamide (1.54 g, 8 mmol) and formaldehyde (2.02 g 37% solution in water, 40 mmol) in acetonitrile (5 ml) is heated at reflux over the weekend. After removal of the solvents, the residue is chromatographed on silica (toluene:ethyl acetate 2:1 v:v) to give the product as a pale yellow solid. $^1$H-NMR (CDCl$_3$, 300 MHz) δ 2.73, 3.17 (AB, $^2$J=18 Hz, CH$_2$O); 4.38, 4.63 (AB, $^2$J=9 Hz, CH$_2$CO); 4.92 (s, 2H, CH$_2$Ph); 6.82 (d, 1H, J=7.4 Hz, Ar ortho-H), 7.08 (tr, 1H, Ar—H); 7.20-7.35 (m, 7H, Ar H). $^{13}$C-NMR (CDCl$_3$, 75 MHz) δ 38.82 (CH$_2$O); 44.58 (CH$_2$CO); 50.58 (q C); 75.07 (CH$_2$Ph); 110.04, 122.64, 123.89 (3 Ar—CH), 127.54 (2 C, Ph CH); 128.16 (Ar CH); 129.16 (2 C, Ph CH); 129.64 (Ar CH); 130.77, 135.40, 142.18 (3 Ar C); 171.37, 175.91 (2 C═O).

Example 29

Preparation of Dimethyl-{2-[5-(4,4,5,5-tetramethyl-[1,3,2]dioxaborolan-2-yl-1H-indol-3-yl]-ethyl}-amine

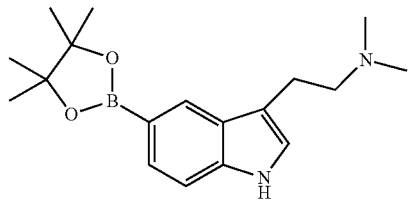

A solution of [2-(5-Bromo-1H-indol-3-yl)-ethyl]-dimethyl-amine (1.069 g, 4 mmol) in dried diethyl ether (25 ml) is prepared under rigorous exclusion of moisture and oxygen.

The solution is cooled to −78° C., and then a solution of t-BuLi (8.0 ml 1.5 N in pentanes, 12 mmol) is added slowly over 10 minutes. A beige suspension is formed, which is stirred at −78° C. for another 15 minutes, and then allowed to warm over 30 minutes to −30° C. The mixture is stirred at −30° C. for another 30 minutes, and then a solution of 2-iso-propoxy-4,4,5,5,-tetramethyl-[1,3,2]dioxaborolane (1.116 g, 6 mmol) in ether (5 mL) is added dropwise within 10 minutes whilst the temperature is maintained in the range between −30 to −25° C. The reaction mixture is stirred for another 30 minutes at −30° C. and then allowed to warm to ambient temperature. After stirring for another 90 minutes, the reaction is quenched by the addition of water (15 ml) and chloroform (30 ml). The organic layer is separated, and washed with brine (15 ml). The aqueous layer is washed with chloroform (15 ml), and from the combined organic layers the solvent is removed on the rotavapor to leave a brown oil (1.5 g) which is chromatographed on silica ($CHCl_3$:MeOH 19:1 v:v) to give the product as an oil (0.193 g, 15.3%). $^1$H-NMR ($CDCl_3$, 300 MHz): δ 1.37 (s, 12H, 4 $CH_3$); 2.36 (s, 6H, N($CH_3$)$_2$); 2.66-2.74 (m, 2H, $CH_2NMe_2$); 2.93-3.02 (m, 2H, $CH_2$); 6.94 (d, J=2.1 Hz, H-2); 7.30 (dd, 1H, J=8.3 Hz, J=0.7 Hz, H-7); 7.60 (dd, 1H, J=8.1 Hz, J=1.0 Hz, H-6 (NOE with 4 $CH_3$)); 8.09 (s, 1H, H-4 (NOE with 4 $CH_3$)); 8.94 (br s, 1H, NH). $^{13}$C-NMR ($CDCl_3$, 75 MHz) δ 23.43 (ArCH$_2$); 25.02 (4 $CH_3$); 45.33 (N($CH_3$)$_2$); 60.15 ($CH_2NMe2$); 83.70 (C(Me)$_2$); 110.86 (C-7); 114.30 (C-3); 121.94 (C-2); 126.59 (C-4); 127.34 (C-9); 128.28 (C-6); 138.64 (C-8) (C-5 not observed). ESI-MS: 315.25 (80%), 316.47 (20%) (MH+).

The invention claimed is:

1. A compound or a salt thereof of formula II shown below

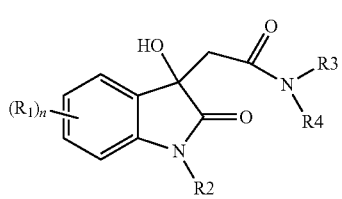

(II)

wherein n is a number from 0 to 4, each $R_1$ is, independently of the other substituents $R_1$, is unsubstituted or substituted alkyl, unsubstituted or substituted aryl, unsubstituted or substituted heterocyclyl, alkylsulfonyl, sulfonyl alkyl, N-mono- or N,N-disubstituted or unsubstituted aminosulfonyl alkyl, hydroxy, mercapto, nitro, halogen, cyano, carboxamido, N-mono- or N,N-disubstituted carboxamido, carboxyhydrazido, unsubstituted or substituted alkoxycarbonyl, unsubstituted or substituted alkoxy, formyl or other alkanoyl, unsubstituted or substituted alkenyl, unsubstituted or substituted alkynyl, unsubstituted or substituted cycloalkyl, alkanoyloxy, N-mono- or N,N-disubstituted or unsubstituted amino, unsubstituted or substituted hydrazino, or is a residue of a boronic acid or an ester thereof, R2 is hydrogen or unsubstituted or substituted alkyl, unsubstituted or substituted alkoxycarbonyl, unsubstituted or substituted arylsulfonyl, unsubstituted or substituted alkylsulfonyl, unsubstituted or substituted aryl, carbamoyl or N-mono- or N,N-disubstituted carbamoyl, silyl substituted by three moieties independently selected from unsubstituted or substituted alkyl and substituted or unsubstituted aryl, or acyl, and R3 and R4 are, independently of each other, unsubstituted or substituted alkyl or together form an unsubstituted or substituted alkylene bridge (thus forming a ring with the binding nitrogen) or an alkylene bridge to which a phenyl or a C3-C8-cycloalkyl ring is condensed at two vicinal carbon atoms of the alkylene bridge.

2. The compound or salt according to claim 1, wherein $R_1$ is nitro, cyano or halogen or a residue of a boronic acid or an ester thereof and n is 1 or 2.

3. The compound or salt according to claim 1 wherein n is an integer from 0 to 3;

each $R_1$ is, independently, lower alkyl; lower alkyl substituted by up to three moieties selected from N,N-di-lower alkylamino, N-phenyl-lower alkylamino, N,N-bis(phenyl-lower alkyl)-amino, N,N-di-lower acylamino, N-lower acylamino, alkylated and/or acylated hydrazino of the formula $R_{20}R_{21}N$—$N(R_{22})$— wherein $R_{20}$ is alkyl or acyl or substituted alkyl and $R_{21}$ is hydrogen or $R_{20}$ and $R_{22}$ is hydrogen or acyl; halo-lower alkyl; $C_3$-$C_{10}$-cycloalkyl; lower alkoxy; aryl-lower alkoxy; lower alkanoyloxy; N,N-di-lower alkylamino; N-phenyl-lower alkylamino, N,N-bis(phenyl-lower alkyl)-amino, N'-phenyl-lower alkylhydrazino, N',N'-bis(phenyl-lower alkyl)-hydrazino, each of which contains phenyl unsubstituted or substituted; N',N'-di-lower alkylhydrazino; unsubstituted or substituted aryl; unsubstituted or substituted heterocyclyl; unsubstituted or lower alkyl substituted and/or mono- or di-oxosubstituted heterocyclenyl or heterocyclyl; alkylsulfonyl; sulfonyl alkyl; unsubstituted, N-mono- or N,N-disubstituted aminosulfonyl alkyl; hydroxy; mercapto; nitro; halogen; cyano; carboxamido or carboxhydrazido; N-mono- or N,N-disubstituted carboxamido; unsubstituted or substituted alkoxycarbonyl; unsubstituted or substituted alkoxy; formyl or other alkanoyl; unsubstituted or substituted alkenyl; unsubstituted or substituted alkynyl;

or $R_1$ is a residue of a boronic acid or an ester thereof;

R2 is hydrogen or unsubstituted or substituted alkyl with substituents as defined for substituted lower alkyl R1; unsubstituted or substituted lower alkoxycarbonyl wherein the substituents are independently selected from lower alkyl and phenyl-lower alkyl; unsubstituted or substituted arylsulfonyl, unsubstituted or substituted alkylsulfonyl; unsubstituted or substituted phenyl; carbamoyl or N-mono- or N,N-disubstituted carbamoyl; silyl substituted by three moieties independently selected from unsubstituted or substituted lower alkyl as defined for unsubstituted or substituted lower alkyl R1 and from substituted or unsubstituted aryl as defined above for R1; or acyl selected from lower alkoxycarbonyl, unsubstituted or substituted aryloxycarbonyl or unsubstituted or substituted aryl-lower alkoxycarbonyl, each with unsubstituted or substituted aryl as defined above for R1, or aryl-carbonyl, aryl-lower alkylcarbonyl or (unsubstituted or substituted lower alkyl)-carbonyl; and R3 and R4 are lower alkyl or R3 and R4 together form a lower alkylene bridge.

4. A method for the manufacture of a compound of the formula I or II defined below, comprising a method for the manufacture of esters of the formula I,

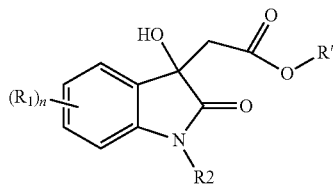

(I)

wherein n is a number from 0 to 4,
each R1 is, independently of the other substituents R1, unsubstituted or substituted alkyl, unsubstituted or substituted aryl, unsubstituted or substituted heterocyclyl, alkylsulfonyl, sulfonyl alkyl, N-mono- or N,N-disubstituted or unsubstituted aminosulfonyl alkyl, hydroxy, mercapto, nitro, halogen, cyano, carboxamido, N-mono- or N,N-disubstituted carboxamido, carboxhydrazido, unsubstituted or substituted alkoxycarbonyl, unsubstituted or substituted alkoxy, formyl or other alkanoyl, unsubstituted or substituted alkenyl, unsubstituted or substituted alkynyl, unsubstituted or substituted cycloalkyl, alkanoyloxy, N-mono- or N,N-disubstituted or unsubstituted amino, unsubstituted or substituted hydrazino, or is a residue of a boronic acid or an ester thereof;
R2 is hydrogen or unsubstituted or substituted alkyl, unsubstituted or substituted alkoxycarbonyl, unsubstituted or substituted arylsulfonyl, unsubstituted or substituted alkylsulfonyl, unsubstituted or substituted aryl, carbamoyl or N-mono- or N,N-disubstituted carbamoyl, silyl substituted by three moieties independently selected from unsubstituted or substituted alkyl and substituted or unsubstituted aryl, or acyl, and
R' is unsubstituted or substituted alkyl,
or of amides of the formula II,

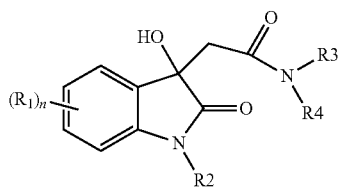

(II)

wherein n, R1 and R2 are as defined under formula I and R3 and R4 are, independently of each other, unsubstituted or substituted alkyl or together form an unsubstituted or substituted alkylene bridge (thus forming a ring with the binding nitrogen) or an alkylene bridge to which a phenyl or a C3-C8-cycloalkyl ring is condensed at two vicinal carbon atoms of the alkylene bridge
where a starting material of the formula III,

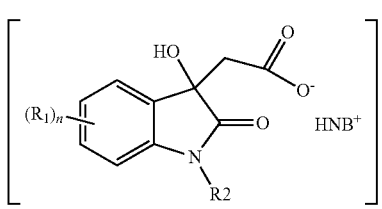

(III)

wherein n, R1 and R2 have the meanings given under formula I and NB is a tertiary nitrogen base where the nitrogen is not part of a ring,
is reacted
(a) for the synthesis of an ester of the formula I with an active carbonic ester of the formula IV,

(IV)

wherein X is halogen and R' is as defined under formula I, to give the corresponding ester of the formula I, or
(b) for the synthesis of an amide of the formula II with an active amido carbonic acid derivative of the formula V,

(V)

wherein X is halogen and R3 and R4 are as defined under formula II, to give the corresponding compound of the formula II,
where in a further step an amide of the formula II wherein n is zero and thus R1 is absent is converted to a compound of the formula VII,

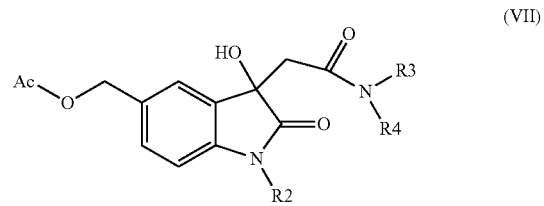

(VII)

wherein Ac is acetyl and R2, R3 and R4 have the meanings indicated for compounds of the formula II with the proviso that in the compound of the formula II and of the formula VII, R2 is other than hydrogen;
by the reaction with formaldehyde or a precursor thereof in the presence of acetic acid, and
transforming the compound of the formula VII

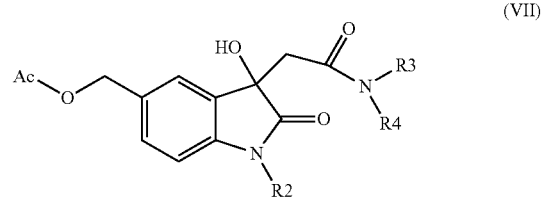

(VII)

into the corresponding free alcohol of the formula VIII,

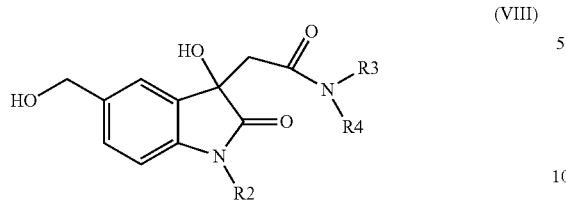

wherein R2, R3 and R4 are as defined under formula VII.

5. The method according to claim 4, further comprising reacting the alcohol of the formula VIII shown in claim 4 with an oxidising agent to give the corresponding compound of the formula IX

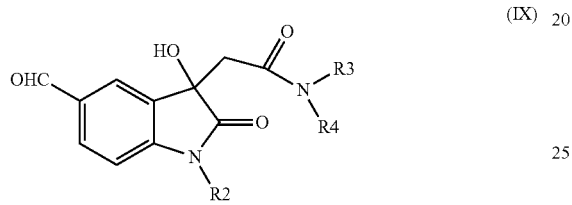

wherein R2, R3 and R4 have the meanings given under formula VII.

6. A method for the manufacture of a compound of the formula I or II defined below, comprising a method for the manufacture of esters of the formula I,

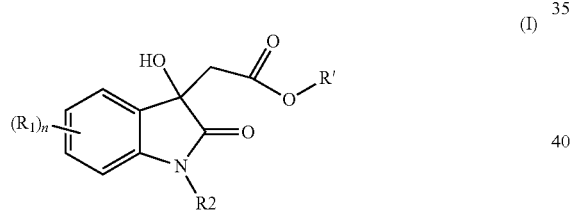

wherein n is a number from 0 to 4,
each R1 is, independently of the other substituents R1, unsubstituted or substituted alkyl, unsubstituted or substituted aryl, unsubstituted or substituted heterocyclyl, alkylsulfonyl, sulfonyl alkyl, N-mono- or N,N-disubstituted or unsubstituted aminosulfonyl alkyl, hydroxy, mercapto, nitro, halogen, cyano, carboxamido, N-mono- or N,N-disubstituted carboxamido, carboxhydrazido, unsubstituted or substituted alkoxycarbonyl, unsubstituted or substituted alkoxy, formyl or other alkanoyl, unsubstituted or substituted alkenyl, unsubstituted or substituted alkynyl, unsubstituted or substituted cycloalkyl, alkanoyloxy, N-mono- or N,N-disubstituted or unsubstituted amino, unsubstituted or substituted hydrazino, or is a residue of a boronic acid or an ester thereof;
R2 is hydrogen or unsubstituted or substituted alkyl, unsubstituted or substituted alkoxycarbonyl, unsubstituted or substituted arylsulfonyl, unsubstituted or substituted alkylsulfonyl, unsubstituted or substituted aryl, carbamoyl or N-mono- or N,N-disubstituted carbamoyl, silyl substituted by three moieties independently selected from unsubstituted or substituted alkyl and substituted or unsubstituted aryl, or acyl, and R' is unsubstituted or substituted alkyl,
or of amides of the formula II,

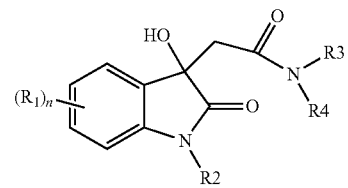

wherein n, R1 and R2 are as defined under formula I and R3 and R4 are, independently of each other, unsubstituted or substituted alkyl or together form an unsubstituted or substituted alkylene bridge (thus forming a ring with the binding nitrogen) or an alkylene bridge to which a phenyl or a C3-C8-cycloalkyl ring is condensed at two vicinal carbon atoms of the alkylene bridge
where a starting material of the formula III,

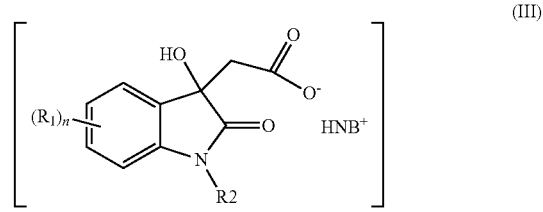

wherein n, R1 and R2 have the meanings given under formula I and NB is a tertiary nitrogen base where the nitrogen is not part of a ring,
is reacted
(a) for the synthesis of an ester of the formula I with an active carbonic ester of the formula IV,

wherein X is halogen and R' is as defined under formula I, to give the corresponding ester of the formula I, or
(b) for the synthesis of an amide of the formula II with an active amido carbonic acid derivative of the formula V,

wherein X is halogen and R3 and R4 are as defined under formula II, to give the corresponding compound of the formula II,
wherein an amide compound of the formula II wherein R2 has one of the meanings given above other than hydrogen is further reacted with a dehydrating agent to give a compound of the formula Xa,

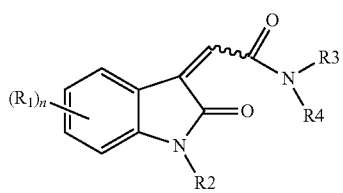

wherein n and R1 are as defined under formula I and R3 and R4 are, independently of each other, unsubstituted or substituted alkyl, or together form an unsubstituted or substituted alkylene bridge, and reducing the compound of the formula Xa in the presence of a reductant to a compound of the formula Xb,

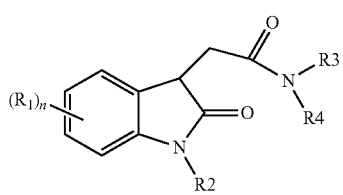

wherein n, R1, R2, R3 and R4 are defined above.

7. The method according to claim 6, wherein the compound of the formula Xb is obtained by hydrogenation of the benzylic 3-hydroxy group in a compound of the formula II.

8. A method for preparing a spiro indole of the formula XI,

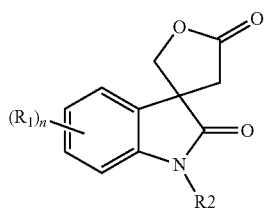

comprising converting a compound of the formula Xb as defined in claim 6 to a spiro indole of the formula XI by reaction with formaldehyde or a precursor thereof, wherein n, R1 and R2 are as defined in claim 6.

9. A method for the manufacture of a compound of the formula I or II defined below, comprising a method for the manufacture of esters of the formula I,

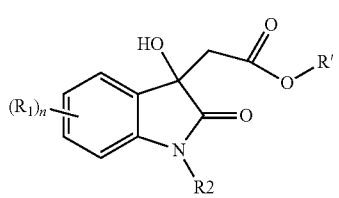

wherein n is a number from 0 to 4,

R1 is unsubstituted or substituted alkyl, unsubstituted or substituted aryl, unsubstituted or substituted heterocyclyl, alkylsulfonyl, sulfonyl alkyl, N-mono- or N,N-disubstituted or unsubstituted aminosulfonyl alkyl, hydroxy, mercapto, nitro, halogen, cyano, carboxamido, N-mono- or N,N-disubstituted carboxamido, unsubstituted or substituted alkoxycarbonyl, unsubstituted or substituted alkoxy, formyl or other alkanoyl, unsubstituted or substituted alkenyl, unsubstituted or substituted alkynyl, unsubstituted or substituted cycloalkyl, alkanoyloxy, N-mono- or N,N-disubstituted or unsubstituted amino, or is a residue of a boronic acid or an ester thereof, R2 is hydrogen or unsubstituted or substituted alkyl, unsubstituted or substituted alkoxycarbonyl, unsubstituted or substituted arylsulfonyl, unsubstituted or substituted alkylsulfonyl, unsubstituted or substituted aryl, carbamoyl or N-mono- or N,N-disubstituted carbamoyl, silyl substituted by three moieties independently selected from unsubstituted or substituted alkyl and substituted or unsubstituted aryl, or acyl, and R' is unsubstituted or substituted alkyl, or of amides of the formula II,

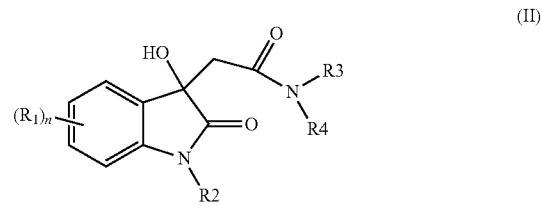

wherein n, R1 and R2 are as defined under formula I and R3 and R4 are, independently of each other, unsubstituted or substituted alkyl or together form an unsubstituted or substituted alkylene bridge (thus forming a ring with the binding nitrogen) or an alkylene bridge to which a phenyl or a C3-C8-cycloalkyl ring is condensed at two vicinal carbon atoms of the alkylene bridge where a starting material of the formula III,

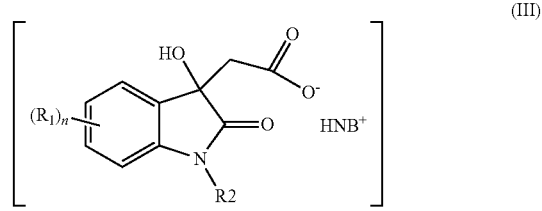

wherein n, R1 and R2 have the meanings given under formula I and NB is a tertiary nitrogen base where the nitrogen is not part of a ring, is reacted (a) for the synthesis of an ester of the formula I with an active carbonic ester of the formula IV,

wherein X is halogen and R' is as defined under formula I, to give the corresponding ester of the formula I, or (b) for the synthesis of an amide of the formula II with an active amido carbonic acid derivative of the formula V,

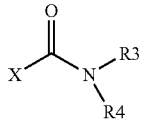
(V)

wherein X is halogen and R3 and R4 are as defined under formula II, to give the corresponding compound of the formula II, the method further comprising reducing a compound of the formula II wherein n, R1, R2, R3 and R4 are, independently of each other, as defined above, in the presence of a complex hydride.

10. The method according to claim 9 wherein as reductant a borane di-lower alkyl sulfide is used, resulting in the formation of the corresponding indole of the formula XII

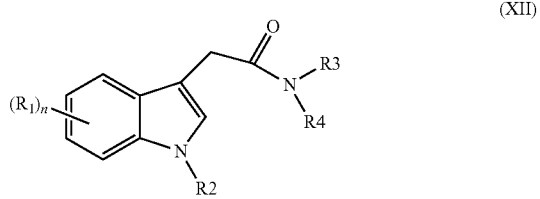
(XII)

wherein the symbols and moieties are as defined in claim 9.

* * * * *